(12) United States Patent
Coles et al.

US007923218B2

(10) Patent No.: US 7,923,218 B2
(45) Date of Patent: Apr. 12, 2011

(54) MODULATION OF THE INTEGRIN LINKED KINASE SIGNALING PATHWAY TO PROMOTE CARDIAC CELL PROLIFERATION AND SELF-RENEWAL

(75) Inventors: John G. Coles, Toronto (CA); Gregory Hannigan, Toronto (CA); Huanzhang Lu, Toronto (CA)

(73) Assignee: John G. Coles, Toronto, Ontario (CA)

( * ) Notice: Subject to any disclaimer, the term of this patent is extended or adjusted under 35 U.S.C. 154(b) by 10 days.

(21) Appl. No.: 11/915,687

(22) PCT Filed: May 29, 2006

(86) PCT No.: PCT/CA2006/000868
§ 371 (c)(1),
(2), (4) Date: Nov. 27, 2007

(87) PCT Pub. No.: WO2006/125321
PCT Pub. Date: Nov. 30, 2006

(65) Prior Publication Data
US 2008/0274491 A1    Nov. 6, 2008

(51) Int. Cl.
*C12Q 1/48* (2006.01)
(52) U.S. Cl. .......................................... 435/15
(58) Field of Classification Search .................. 435/15
See application file for complete search history.

(56) References Cited

U.S. PATENT DOCUMENTS

| 6,013,782 | A | 1/2000 | Dedhar et al. |
| 6,699,983 | B1 | 3/2004 | Dedhar et al. |
| 2004/0220125 | A1* | 11/2004 | Coles et al. ................. 514/44 |
| 2005/0054599 | A1* | 3/2005 | Coles et al. ................. 514/44 |
| 2006/0121496 | A1 | 6/2006 | Srivastava et al. .......... 435/6 |
| 2008/0214799 | A1* | 9/2008 | Coles et al. ............... 536/23.5 |

FOREIGN PATENT DOCUMENTS

| CA | 2609937 | 11/2006 |
| CA | 2610521 | 11/2006 |
| WO | WO 2006/125321 | 11/2006 |
| WO | WO 2006/125322 | * 11/2006 |
| WO | WO 2007/137414 | 12/2007 |

OTHER PUBLICATIONS

Bock-Marquette I. et al. Thymosin Beta4 Activates Integrin Linked Kinase and Promotes Cardiac Cell Migration, Survival and Cardiac Repair. Nature vol. 432, pp. 466-472, Nov. 25, 2004.*
Pham C. et al. Striated Muscle Specific Beta 1D Integrin and FAK are Involved in Cardiac Myocyte Hypertrophic Response Pathway. Am J Physiol Heart Circ Physiol 279:2916-2926, 2000.*
Anversa P, et al., "Myocyte renewal and ventricular remodelling." Nature,415: pp. 240-243 (2002).
Araki H, et al. "Expansion of human umbilical cord blood SCID-repopulating cells using chromatin-modifying agents." Exp Hexnatol., 34: pp. 140-149 (2006).
Austin TW, et al., "A role for the Wnt gene family in hematopoiesis: expansion of multilineage progenitor cells." Blood 89: No. 10: pp. 3624-3635 (1997).
Beltrami AP, et al., "Adult cardiac stem cells are multipotent and support' myocardial regeneration." Cell, pp. 114: pp. 763-776 (2003).
Choi JH, et al., "Augmentation of Therapeutic Angiogenesis Using Genetically Modified Human Endothelial Progenitor Cells with Altered Glycogen Synthase Kinase-3β Activity." J Biol Chem., 279: No. 47: pp. 49430-49438 (2004).
Coles JG, et al.,"Cardioprotective stress response in the human fetal heart." JTCVS, 129: pp. 1128-1136 (2005).
Eckfeldt CE, et al., "The molecular repertoire of the 'Almighty' stem cell." Nature, vol. 6: Nat Rev Mol Cell Biol., pp. 726-737 (2005).
Gerber HP, et al., "VEGF regulates haematopoietic stem cell survival by an internal autocrine loop mechanism." Nature, 417: pp. 954-958 (2002).
Hannigan GE, et al., "Regulation of cell adhesion and anchorage-dependent growth by a new beta 1integrin-linked protein kinase." Nature, 379: pp. 91-96 (1996).
Hannigan G, et al., "Integrin-linked kinase: a cancer therapeutic target unique among its ILK." Nat Rev Cancer,5: pp. 51-63 (2005).
Konstantinov IE, et al. "Gene expression profiles in children undergoing cardiac surgery for right heart obstructive lesions." J Thorac Cardiovasc Surg.,vol. 127: No. 3: pp. 746-754 (2004).
Kumar AS, et al., "ILKAP regulates ILK signaling and inhibits anchorage-independent growth." Oncogene, 23: pp. 3454-3461 (2004).
Laugwitz KL, et al., "Postnatal isl1+ cardioblasts enter fully differentiated cardiomyocyte lineages." Nature, vol. 433: pp. 647-653 (2005).
Lee A, et al., "Isolation of neural stem cells from the postnatal cerebellum." Nature Neuroscience, vol. 8: pp. 723-729 (2005).
Leung-Hagesteijn C, et al., "Modulation of integrin signal transduction by ILKAP, a protein phosphatase 2C associating with the integrinlinked kinase, ILK1." EMBO J., vol. 20: No. 9: pp. 2160-70 (2001).
Liu BY et al., "The transforming activity of Wnt effectors correlates with their ability to induce the accumulation of mammary progenitor cells." Proc Natl Acad Sci USA, vol. 101: No. 12: pp. 4158-4163 (2004).
Matsuura K, et al., "Adult cardiac Sea-1-positive cells differentiate into beating cardiomyocytes." J Biol Chem., vol. 279: No. 12: pp. 11384-11391 (2004).
Messina E, et al. "Isolation and expansion of adult cardiac stem cells from human and murine heart." Circ Res., 95: pp. 911-921 (2004).

(Continued)

*Primary Examiner* — Ralph Gitomer
(74) *Attorney, Agent, or Firm* — Vedder Price P.C.; Ajay A. Jagtiani

(57) ABSTRACT

Modulation of the integrin-linked kinase (ILK) signaling pathway is used to enhance the remodeling process relevant to a wide range of cardiac diseases. More specifically, a process to instigate beneficial human cardiac hypertrophy or for post myocardial infarction (MI) remodeling comprising illiciting an overexpression of ILK, is described. The ILK signaling pathway is also used as a means for cardiac stem cell proliferation and self-renewal.

35 Claims, 17 Drawing Sheets

OTHER PUBLICATIONS

Miller MG, et al., "Integrin-linked kinase is a positive mediator of L6 myoblast differentiation." *Biochem Biophys Res Commun.*,310: pp. 796-803 (2003).

Milosevic J. et al., "Cyropreservation does not affect proliferation and multipotency of murine neural precursor cells." *Stem Cells*, 23: pp. 681-688 (2005).

Nelson W. et al., "Convergence of Wnt, beta-catenin, and cadherin pathways." *Science*,.vol. 303: pp. 1483-1487 (2004).

Novak A, et al., "Cell adhesion and the integrin-linked kinase regulate the LEF-1 and beta-catenin signaling pathways." *Proc Natl Acad Sci USA*, vol. 95: pp. 4374-4379 (1998).

Novak A, et al., "Signaling through beta-catenin and Lef/Tcf." *Cell Mol Life Sci*, 56: pp. 523-537 (1999).

Oh H, et al., "Cardiac muscle plasticity in adult and embryo by heart-derived progenitor cells." *Ann NY Acad Sci.*,1015: pp. 182-189 (2004).

Persad S, et al., Inhibition of integrin-linked kinase (ILK) suppresses activation of protein kinase B/Akt and induces cell cycle arrest and apoptosis of PTEN-mutant prostate cancer cells. *Proc Natl Acad Sci USA,*; vol. 97: No. 7: pp. 3207-3212 (2000).

Reya T, et al., "Wnt signalling in stem cells and cancer." *Nature*, vol. 434: pp. 843-850 (2005).

Reya T, et al., "A role for Wnt signalling in self renewal of haematopoietic stem cells." *Nature*, vol. 423: pp. 409-414 (2003).

Sato N. et al., "Maintenance of pluripotency in human and mouse embryonic stem cells through activation of Wnt signaling by a pharmacological GSK-3-specific inhibitor." *Nat Med*,.vol. 10: pp. 55-63 (2004).

Tan C, et al., "Inhibition of integrin linked kinase (ILK) suppresses beta-cateninLef/Tcf-dependent transcription and expression of the E-cadherin repressor, snail, in APC-/- human colon carcinoma cells." *Oncogene*, vol. 20: pp. 133-140 (2001).

Troussard AA, et al., Cell-extracellular matrix interactions stimulate the AP-1 transcription factor in an integrinlinked kinase- and glycogen synthase kinase 3dependent manner.: *Mol. Cell. Biol.*,vol. 19: No. 11: pp. 7420-7427 (1999).

Troussard AA, et al. "Conditional knock-out of integrin-linked kinase demonstrates an essential role in protein kinase B/Akt activation." *J Biol Chem.*,vol. 278: No. 25: pp. 22374-22378 (2003).

Xie D, et al., "Cyr61 is overexpressed in gliomas and involved in integrin-linked kinase-mediated Akt and beta-catenin-TCF/Lef signaling pathways." *Cancer Res,*.64: pp. 1987-1996 (2004).

Yamataka A, et al., "Abnormal distribution of intestinal pacemaker (C-KIT-positive) cells in an infant with chronic idiopathic intestinal pseudoobstruction.", *J Pediatr Surg*; vol. 33: No. 8: pp. 859-862 (1998).

Zechner D, et al., "β-Catenin signals regulate cell growth and the balance between progenitor cell expansion and differentiation in the nervous system." *Dev Biol.*, 258: pp. 406-418 (2003).

Freund, C. et al. "Requirement of nuclear factor kappaB in angiotensin II- and isoproterenol-induced cardiac hypertrophy in vivo", *Circulation*, 111: p. 2319-2325 (2005).

Kee, HJ et al., "Inhibition of histone deacetylation blocks cardiac hypertrophy induced by angiotensin II infusion and aortic banding." *Circulation*, 113: pp. 51-59 (2006).

Wu et al., "Integrin-linked kinase (ILK) and its interactions: a new paradigm for the coupling of extracellular matrix to actin cytoskeleton and signaling complexes." *J. Cell Biology*, 155 (4). pp. 505-510 (2001).

\* cited by examiner

MODULATION OF THE INTEGRIN LINKED KINASE SIGNALING PATHWAY TO PROMOTE CARDIAC CELL PROLIFERATION AND SELF-RENEWAL

CROSS REFERENCE TO RELATED APPLICATIONS

This application is a U.S. national-stage patent application from international application PCT/CA06/000868, filed May 29, 2006, which claims the benefit of priority to U.S. Provisional Patent Application No. 60/685,269, filed May 27, 2005. The contents and disclosure of these application(s) are hereby incorporated by reference in their entirety.

FIELD OF THE INVENTION

This invention relates generally to the benefits of elevated expression of Integrin Linked Kinase (ILK), particularly to the cardioprotective effect evidenced as a result of upregulation of ILK post myocardial infarction, and most particularly to ILK mediated reduction of infarct size and beneficial increase in left ventricular mass post MI and to use of ILK as a means for cardiac stem cell proliferation and self-renewal.

BACKGROUND OF THE INVENTION

The major barrier to the use of stem cell therapy in regenerative medicine is the inability to regulate the dichotomous capacity for stem cell self-renewal versus the process of cell lineage commitment. The solution to this problem will require an improved understanding of the inductive signals and the cognate signal transduction pathways which determine cellular fate, and which specifically govern the competitive outcomes of self-renewal with maintenance of pluripotency, versus differentiation into a specialized tissue phenotype[i].

The evolutionarily conserved canonical Wnt pathway has been implicated in both human and mouse embryonic stem (ES) cell self-renewal competence[ii]. Inactivation of glycogen synthase kinase-3β (GSK-3β) leads to nuclear accumulation of β-catenin, which, in turn, leads to the activation of Wnt target genes implicated in the proliferation of endothelial precursor cells[iii], and in self-renewal of HESCs[iv].

ILK is a protein Ser/Thr kinase that binds to the cytoplasmic domains of β1, β2 and β3-integrin subunits[v]. ILK is regulated in a phosphoinositide 3'-kinase (PI3K)-dependent manner following distinct signal inputs from integrins and growth factor receptor tyrosine kinases[vi,vii]. Conditional knockdown and RNA interference experiments indicate that ILK is required for phosphorylation of PKB/Akt Ser473 and GSK-3β Ser9[viii]. Since inhibitory phosphorylation of GSK-3β is sufficient for maintenance of an undifferentiated phenotype in mouse and human ESCs, ILK is a candidate kinase activator of a critical stem cell signaling cascade.

We have shown that cardiac-restricted ILK over-expression in a mouse model causes a compensatory (beneficial) form of cardiac hypertrophy. Molecular analysis revealed that ILK mediated hypertrophy is dependent upon a novel pathway involving activation of the small G-protein, Rac1. Gene expression profiling of ILK transgenic mice subjected to LAD ligation-induced myocardial infarction revealed up-regulation of transcripts linked to IL-6 and Janus-associated tyrosine kinase/signal transducer of activated transcription (JAK/STAT3) signaling. These studies establish ILK as an important new cardiovascular target. The activation of these signaling cascades in this myocardial injury model should be stimulative to stem cell recruitment based on their established role in cell renewal in mouse ESCs.

We anticipate that fetal sources of tissue will be enriched for stem cells, given that stem cell activation recapitulates fetal programming. We have developed and characterized an in vitro model of human fetal cardiac myocytes (HFCM)[ix], and characterized the genomic response to ischemic stress during human heart surgery in vivo[x]. We have shown that cardiac stem-like cells can be identified by c-kit staining in HFCM with a frequency approximately one order of magnitude higher than that described for adult heart[xi]. Further, we have shown that ILK gain-of-function increases the frequency of c-kit- and CD133-positive cardiac progenitor cells isolated from human myocardium, highlighting this as a rational approach to augment stem cell-based cellular therapy.

Ventricular hypertrophy is an extremely common clinical condition that appears as a consequence of any variety of volume and or pressure overload stresses on the human heart. An increase in ventricular mass occurring in response to increased cardiac loading is generally viewed as a compensatory response, which serves to normalize ventricular wall tension and improve pump function. Conversely, a sustained or excessive hypertrophic response is typically considered maladaptive, based on the progression to dilated cardiac failure sometimes observed clinically, and the statistical association of ventricular hypertrophy with increased cardiac mortality. Whereas mouse models of cardiac hypertrophy have been generated by genetically-induced alterations in the activation state of various kinases in the heart, limited information is available regarding the role of specific signaling pathways activated during human ventricular hypertrophy.

The identification of the kinase pathways implicated in human hypertrophy has important therapeutic implications, since it will allow testing of the hypothesis that enforced hypertrophy induction represents a beneficial remodeling response, and a useful strategy to preserve cardiac function and arrest the transition to a dilated phenotype.

DESCRIPTION OF THE PRIOR ART

U.S. Pat. Nos. 6,013,782 and 6,699,983 are directed toward methods for isolating ILK genes. The patents suggest that modulation of the gene activity in vivo might be useful for prophylactic and therapeutic purposes, but fails to teach or suggest any perceived benefit relative to over or under expression of ILK with respect to cardiac hypertrophy or post MI cardiac remodeling.

SUMMARY OF THE INVENTION

An increase in hemodynamic wall stress (also termed afterload) due to impedance to outflow of blood from either the right or left ventricle can result in concentric cardiac hypertrophy of the affected ventricle. Diseases affecting intrinsic cardiac function, such as coronary artery disease or various forms of cardiomyopathy, may indirectly increase afterload, and lead to a hypertrophic response involving the residual, non-diseased myocardium.

Integrins have been implicated as a component of the molecular apparatus which serves to transduce biomechanical stress into a compensatory growth program within the cardiomyocyte, based on their role in linking the extracellular matrix (ECM) with intracellular signaling pathways affecting growth and survival. Melusin is a muscle protein that binds to the integrin β1 cytoplasmic domain and has been identified as a candidate mechanosensor molecule in the heart. Experimental aortic constriction in melusin-null mice results in an impaired hypertrophic response through a mechanism involving reduced phosphorylation of glycogen synthase kinase-3β (GSK3β), which inhibits a key nodal regulator of cardiac hypertrophic signaling. The role of melusin or other potential molecules participating in the endogenous hypertrophic response to disease-induced cardiac hypertrophy in humans, however, remains unknown.

Integrin-linked kinase (ILK) is a protein Ser/Thr kinase that binds to the cytoplasmic domains of β1, β2 and β3-integrin subunits. ILK serves as a molecular scaffold at sites of integrin-mediated adhesion, anchoring cytoskeletal actin and nucleating a supramolecular complex comprised minimally of ILK, PINCH and β-parvin. In addition to its structural role, ILK is a signaling kinase coordinating cues from the ECM in a phosphoinositide 3'-kinase (PI3K)-dependent manner following distinct signal inputs from integrins and growth factor receptor tyrosine kinases. ILK lies upstream of kinases shown in experimental models to modulate hypertrophy, and is required for phosphorylation of protein kinase B (Akt/PKB) at Ser473 and GSK3β at Ser9. Rho-family guanine triphosphatases (GTPases, or G-proteins), including RhoA, Cdc42, and Rac1, modulate signal transduction pathways regulating actin cytoskeletal dynamics in response to matrix interaction with integrin and other cell surface receptors. Both RhoA and Rac1 have been shown to modulate cardiac hypertrophy. ECM adhesion stimulates the increased association of activated, GTP-bound Rac1 with the plasma membrane, suggesting a role for ILK in promoting membrane targeting of activated Rac1. ILK may also activate Rac1 through regulated interaction of the Rac1/Cdc42 specific guanine-nucleotide exchange factor (GEF), ARHGEF6/-PIX, with β-parvin, an ILK-binding adaptor, as occurs during cell spreading on fibronectin. ILK is thus positioned to functionally link integrins with the force-generating actin cytoskeleton, and is a candidate molecule in the transduction of mechanical signals initiated by altered loading conditions affecting the heart.

The instant invention demonstrates that ILK protein expression is increased in the hypertrophic human ventricle, and further demonstrates that ILK expression levels correlate with increased GTP loading, or activation, of the small G-protein, Rac1. Transgenic mice with cardiac-specific activation of ILK signaling are shown to exhibit compensated LV hypertrophy. In agreement with the findings in the human hypertrophic heart, ventricular lysates derived from ILK over-expressing mice lines exhibit higher levels of activated Rac1 and Cdc42, in association with activation of p38 mitogen-activated protein (p38MAPK) and ERK1/2 kinase cascades.

Additionally, increased ILK expression is shown to enhance post-infarct remodeling in mice through an increased hypertrophic response in myocardium remote from the lesion. The transgenic models indicate that ILK induces a program of pro-hypertrophic kinase activation, and suggest that ILK represents a critical node linking increased hemodynamic loading to a cardioprotective, hypertrophic signaling hierarchy. Moreover, the ILK transgenic mouse is shown to provide a new model of cardiac hypertrophy that is highly relevant to human cardiac disease.

Protein kinases are increasingly understood to be important regulators of cardiac hypertrophy, however the critical question arises of whether kinases known to induce experimental hypertrophy are, in fact, up-regulated or activated as a feature of human cardiac hypertrophy. The instant invention unequivocally demonstrates increased expression and activity of a candidate mechano-sensor/transducer, namely ILK, in human cardiac hypertrophy.

Moreover, it is shown that moderate up-regulation of ILK in the myocardium of transgenic mice causes a compensated form of cardiac hypertrophy, as evidenced by unimpaired survival, preserved systolic and diastolic function, and the absence of histopathological fibrosis. Among a number of hypertrophy-inducing protein kinases that were examined, only two, ILK and PKB, demonstrated elevated protein levels in association with hypertrophy. Of these, ILK was consistently elevated in both congenital and acquired hypertrophies. Importantly, in consequence of ILK expression, transgenic myocardium exhibited a strikingly similar profile of protein kinase activation, to that seen in human cardiac hypertrophy. The fact that ILK up-regulation is associated with mechanical load-induced hypertrophy (secondary to congenital and acquired forms of outflow tract obstruction), in which global cardiac function was preserved, provides compelling evidence that ILK activation is associated with a provokable, compensatory form of hypertrophy in the human heart. At the molecular level, the human and mouse data included herein suggest that ILK is a proximal mechanotransducer, acting to coordinate a program of "downstream" hypertrophic signal transduction in response to pressure overload in the myocardium.

The lack of Akt/PKB and GSK3β phosphorylation in ILK over-expressing mice was unexpected, given that ILK is regulated in a PI3K-dependent manner, and has been shown to directly phosphorylate both target kinases in non-cardiomyocytes 10, 12, 13, 14, and contrasts with findings from genetic models of cardiac-specific PI3K and Akt/PKB activation, which feature increased phosphorylation of both Akt/PKB and GSK3β in proportion to the degree of hypertrophy. We note, however, that levels of PKB Ser473 and GSK-3β Ser9 phosphorylation are quite high in both murine and human control hearts, consistent with the requirement for a threshold basal level of activation of theses kinases, which may be permissive to the induction of ILK-mediated hypertrophic signaling. Our results are thus consistent with operation of a p110/ILK/Rac1 pathway, but suggest that the ILK-specific hypertrophy is not critically dependent upon increased phosphorylation of PKB/Akt or GSK3β. The relative de-activation of Akt/PKB during ILK transgenesis is consistent with the finding that activation of Akt/PKB and inhibitory phosphorylation of GSK3β occur in advanced failure, but not during compensated hypertrophy, in human hearts. Thus, the lack of highly activated Akt/PKB in murine and human hearts exhibiting elevated ILK expression may be a signature of compensated hypertrophy.

Our results in transgenic mice with ILK over-expression, as well as in human hypertrophy, reveal the selective activation of ERK1/2 and p38 signaling pathways, despite evidence for the relative deactivation of PI3K-dependent signaling through Akt/PKB and GSK3β. Genetic stimulation of the ERK1/2 branch of the MAPK signaling pathway has been shown previously to be associated with a physiological hypertrophic response and augmented cardiac function. S6 kinases promote protein translation by phosphorylating the S6 protein of small ribosomal subunits, and are required for mammalian target of rapamycin (mTOR)-dependent muscle cell growth. Activation of p70 ribosomal protein S6 kinase (p70S6K) provides a potential pathway mediating ILK-triggered myocyte hypertrophy which is independent of the Akt/PKB pathway. Indeed, ILK is sufficient to regulate the integrin-associated activation of Rac1 and p70S6K, leading to actin filament rearrangement and increased cellular migration. Considered together, our results indicate conservation of downstream signaling specificity resulting from ILK activation in both murine and human hypertrophy. Full elucidation of the unique network of effectors induced during ILK gain-of-function is accomplished by application of high-throughput functional proteomic approaches to genetic models, as well as to stage-specific human diseases characterized by hypertrophic remodeling.

The reciprocal pattern of activation of Rac1 and de-activation of Rho is well-precedented and reflects opposing effects of these monomeric GTPases on the cytoskeleton at the leading edge of migrating cells. Similarly, our results show reciprocal effects both in vitro and in vivo on the activation of Rac1/Cdc42 and Rho in response to ILK upregulation. These data are thus consistent with the observation that transgenic mice over-expressing RhoA develop a predominantly dilated cardiomyopathic phenotype which is antithetical to that observed with ILK activation.

Our data indicates that hemodynamic loading secondary to infarct induction in ILK$^{S343D}$ Tg mice provoked a stress response, which resulted in a larger increase in LV mass and smaller infarct size relative to control. The mechanism(s) accounting for the post-infarction cardioprotective effects of ILK activation require further study, but our result is consistent with the report that thymosin β4 improves early cardiomyocyte survival and function following LAD ligation through a pathway shown to be dependent upon increased ILK protein expression. One putative explanation for the cardioprotective effect of ILK activation in this model is the reduction in wall stress secondary to the observed ILK-potentiated hypertrophic response. The importance of reactive hypertrophy of remote myocardium in limiting wall stress and adverse remodeling after MI has been shown both in patients, and in mice with loss-of-function mutations in pro-hypertrophic, calcineurin-dependent signaling pathways. Further, ILK/Rac1 activation in cardiac myofibroblasts may plausibly promote more efficient scar contraction through mechanisms related to effects on the actin cytoskeleton, which favor a more contractile, motile and invasive cellular phenotype.

In summary, our results identify a novel role for ILK-regulated signaling in mediating a broadly adaptive form of cardiac hypertrophy. The effects of small molecule inhibitors of ILK demonstrated experimentally suggest that this pathway is therapeutically tractable, and together with our results, that modulation of the ILK pathway warrants evaluation as a novel approach to enhance the remodeling process relevant to a wide range of cardiac diseases.

Accordingly, it is a primary objective of the instant invention to teach a process for instigating beneficial human hypertrophy as a result of overexpression of ILK.

It is a further objective of the instant invention to teach a beneficial protective process for post MI remodeling as a result of ILK overexpression.

It is yet another objective of the instant invention to teach a control for instigating ILK overexpression. The objective is to evaluate the capacity of ILK gain-of-function to promote stem cell self-renewal. This objective can be evaluated in a range of cell types derived from ESCs, fetal and adult tissue, available in our Lab and the NRC. Of interest will be the effect of modulation of ILK signaling amplification on stem cell frequency, and on cellular fate, focusing on self-renewal, multilineage differentiation, and the potential for oncogenesis. A major objective of the project is the development of novel methods for the identification, amplification and differentiation of cardiac stem cells. These studies will take into account the effect of instructive (extra-cellular) environmental cues on intra-cellular signal transduction events. The generic pro-survival effect of ILK up-regulation is predicted to enhance cellular transplantation survival, and this important effect can be evaluated in therapeutically relevant in vivo and in vitro models. ILK-based protocols will be investigated both as standalone strategies, and in conjunction with anti-oxidant strategies developed at the NRC.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Methods

Generation of α-MHC-ILK Transgenic Mice

Figure 4:
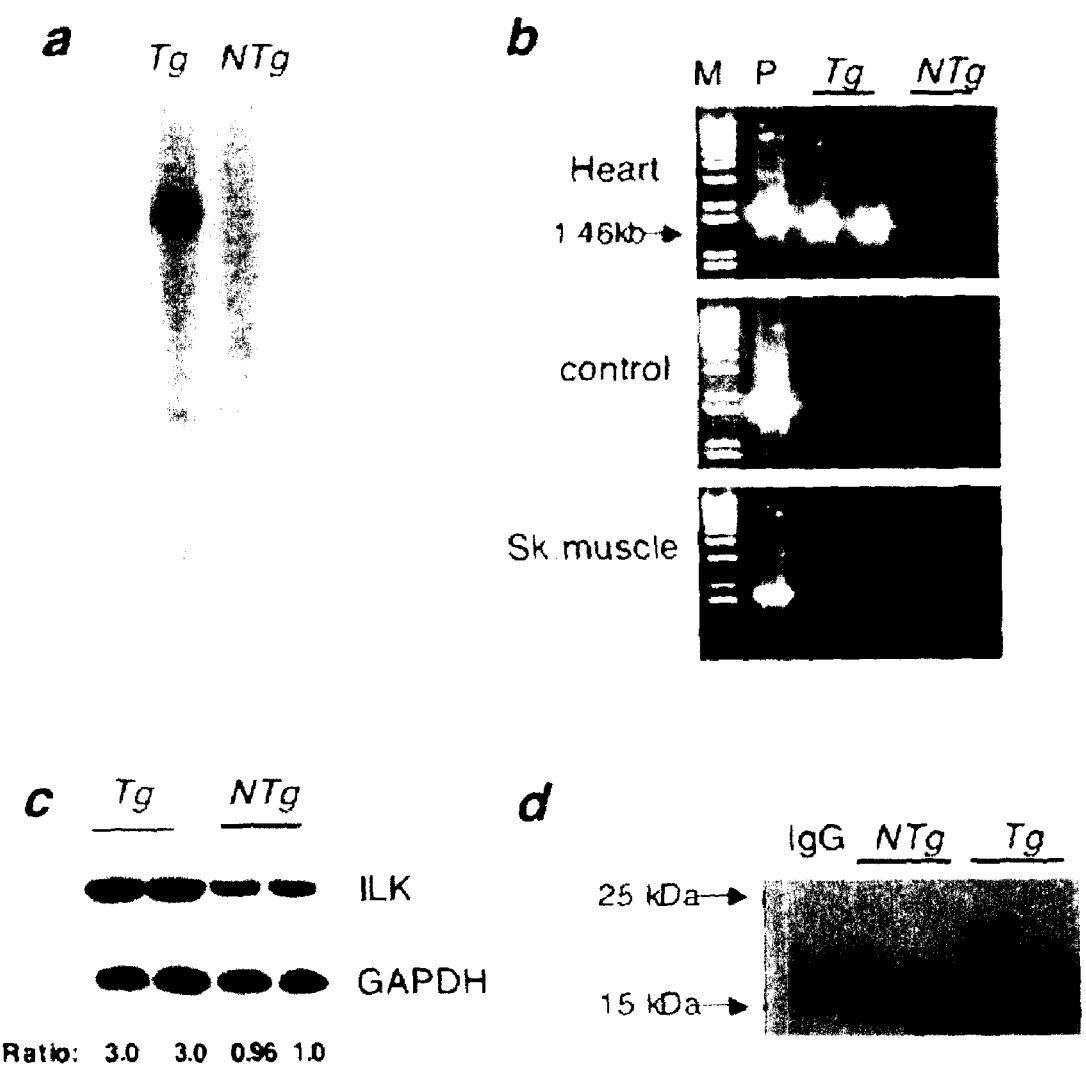
FIG. 4: Characterization of ILK$^{S343D}$ transgenic mice: a, Genomic DNA from ILK$^{S343D}$ Tg and NTg littermates was analyzed by Southern blotting using a human ILK cDNA probe. b, ILK-specific RT-PCR of total RNA isolated from heart tissue with (upper panel) or without (control, middle panel) reverse transcriptase, and on skeletal muscle (bottom panel) with reverse transcriptase. This yields the expected product 1.46 kb in length, expressed in the hearts of Tg mice, but not in the hearts of NTg littermates or skeletal muscle of the Tg mice. The lane marked 'P' is the PCR product obtained using α-MHC/ILK plasmid as template. This product is larger than 1.46 kb because the PCR primers encompass exons 1 and 2 of the α-MHC promoter. c, Western immunoblot analysis of ILK protein levels in ILK Tg and control (NTg) hearts. Signal densities normalized to that of GAPDH were 3-fold higher in ILK Tg hearts. d, ILK immune complex kinase assays of heart lysates from ILK$^{S34D}$ Tg and NTg littermates. Purified myosin light chain II, 20 kDa regulatory subunit was added as exogenous substrate.

All protocols were in accordance with institutional guidelines for animal care. All procedures and analyses were performed in a fashion blinded for genotype, and statistical comparisons were made between ILK transgenic mice and sex-matched littermate non-transgenic mice. A 1.8 kb EcoRI fragment comprising the full length ILK cDNA was excised from a pBSK plasmid, and filled-in for blunt end ligation into a SalI site downstream of the murine a-myosin heavy chain promoter. Site directed mutagenesis (QuickChange Kit, Stratagene) was performed to generate constitutively active ILK (S343D), and kinase-inactive ILK (R211A) mutants using the wild type a-MHC/ILK plasmid as template. DNA sequencing confirmed the point mutations. Pronuclear microinjection of the linearized a-MHC/ILK plasmids into 0.5 day fertilized embryos was performed at the Core Transgenic Facility of the Hospital for Sick Children Research Institute. Transgene expression in C57BL/6 founder and F1 progeny mice was confirmed by Southern analysis and RT-PCR as described, using primers specific for the exogenous ILK transgene. The forward primer: 5'GTCCACATTCTTCAG-GATTCT3', specific for exon 2 of –MHC promoter, and the ILK-specific reverse primer: 'ACACAAGGGGAAATACC GT3', were used for the reaction. These primers amplify a 1460 bp across the α-MHC-ILK fusion junction. F1 progeny derived from one of several independent founder lines were selected for detailed phenotypic analysis based on readily discernible increases in ILK expression (FIG. 4). All transgenic mouse procedures were performed in conformance with the policies for humane animal care governing the Core Transgenic Facility of the Hospital for Sick Children Research Institute and the Animal Research Act of Ontario.

Cardiac Hemodynamic Measurements

All surgical procedures were performed in accordance with institutional guidelines. Mice were anesthetized in the supine position using ketamine-HCl (100 mg/kg ip) and xylazine-HCl (10 mg/kg ip), and maintained at 37° C. The right common carotid artery was isolated after midline neck incision and cannulated using a Millar Micro-tip pressure transducer (1.4F sensor, 2F catheter; Millar Instruments, Houston, Tex.). Heart rate (beats per minute), systolic and diastolic LV pressures (mm Hg) were recorded, and peak positive and negative first derivatives (maximum/minimum+/−dp/dt; mmHg/second) were obtained from LV pressure curves using Origin 6.0 (Microcal Software, Inc., Northampton, Mass.).

Two-Dimensional Echocardiography

Serial two-dimensional echocardiography (2-D echo) was performed in male ILK transgenic and non-transgenic littermate mice at 10-12 weeks, at 5, and 15 months of age. An ultrasound biomicroscope (UBM) (VS40, VisualSonics Inc., Toronto) with transducer frequency of 30 MHz was used to make M-mode recordings of the LV. Mice were lightly anesthetized with isoflurane in oxygen (1.5%) by face mask, and warmed using a heated pad and heat lamp. Heart rate and rectal temperature were monitored (THM100, Indus Instruments, Houston, Tex.) and heating adjusted to maintain rectal temperature between 36 and 38° C. Once anesthetized, the mouse precordial region was shaved and further cleaned with a chemical hair-remover to minimize ultrasound attenuation. With the guidance of the two-dimensional imaging of the UBM, M-mode recording of left ventricular wall motion was obtained from the longitudinal and short axis views of the LV at the level with the largest ventricular chamber dimension. Anterior and posterior LV free wall thickness, and ventricular chamber dimensions were measured at end-systole and end-diastole; the contractility indices, velocity of circumferential fiber shortening (Vcf) and % fractional shortening, and LV ventricular mass, were calculated as described. Determination of significant, genotype-specific differences in 2-D echo and cardiac catheterization data relied on a paired t-test or ANOVA in the case of serial measurements.

ILK Immune Complex Kinase Assay

Cells were lysed in NP40 buffer, supplemented with 1 mM sodium orthovanadate and 5 mM sodium fluoride as phosphatase inhibitors. Equal amounts of protein from these cell lysates were immunoprecipitated with –ILK polyclonal antibody as previously described 10, and immune complexes were incubated at 30 C for 30 min with myosin light chain II regulatory subunit (MLC20) (2.5 g/reaction) and [32P] ATP (5 Ci/reaction). The reactions were stopped by addition of 4× concentrated SDS-PAGE sample buffer. Phosphorylated proteins were separated on 15% SDS-PAGE gels. [32P]MLC20 was visualized by autoradiography with X-Omat film.

Rho Family GTPase Activation Assays

Measurement of activated RhoA was performed using a pull-down assay based on specific binding of Rho-GTP to Rho-binding domain (RBD) of the Rho effector molecule, rhoketin43. Cdc42 and Rac1 activation were measured using a pull-down assay, based on the ability of the p21-binding domain of p21 associated kinase (PAK) to affinity precipitate Rac1-GTP and Cdc42-GTP, as described. RBD expressed as a GST fusion protein bound to the active Rho-GTP form of Rho was isolated using glutathione affinity beads according the manufacturer's protocol (Cytoskeleton). The amount of activated Rho was determined by Western blot using a Rho-specific antibody (Santa Cruz) and normalized as a ratio to the total amount of anti-Rho antibody detected in a ½0 fraction of clarified lysate. Activated Rac and Cdc42 were measured by the same protocol using the p21-binding domain of PAK to affinity precipitate Rac-GTP, which was quantitated using an anti-Rac antibody (Cytoskeleton, Inc.) or anti-Cdc42 (Santa Cruz). Blots were developed with SuperSignal West Femto substrate (Pierce) for the GST-PAK/RBD pull-down assays.

Histopathology

The hearts were weighed, paraffin-embedded, sectioned at 1 mm intervals, and stained with hematoxylin and eosin and Sirius Red using standard methods. Micrographs were taken using both low magnification (×2.5) and higher magnification (×40) using fluorescent microscopy and genotype-specific cardiomyocyte areas determined based on digital measurements of >500 cells per animal and 5 animals per genotype using Image J software (http://rsb.info.nih.gov/ij/). Scanning electron microscopy was performed on ventricular samples placed in 1% Universal fixative for several hours at 4° C. and post-fixed in OsO4, using the JSM 6700FE SEM microscope.

Infarct Induction

LV infarction was created in 6 month ILK TgS343D and littermate control mice by LAD ligation as described. Planimetric scar dimensions measured in six levels of hematoxylin and eosin-stained cross-sections of the LV at 7 days post-infarction.

Antibodies, and Immunoblot Analyses for Total and Phospho-Protein Levels

Total and phospho-specific protein expression was measured in lysates derived from human fetal cardiomyocytes in culture and from transgenic and control mouse ventricular tissue as described previously. Immunoblotting was performed with the following commercially available antibodies. Polyclonal rabbit antibodies against ILK, p38MAPK, p70S6K, p44/42 MAPK (ERK1/2), and ATF-2 were purchased from Cell Signaling Technologies. Phospho-specific antibodies of pp 38MAPK (Thr180/Tyr182), pp70S6K (Thr421/Ser424), pPKB (Ser473), pGSK3B (Ser9), pp 44/42 MAPK (Thr202/Tyr204), and pATF-2 (Thr69/71) were purchased from Cell Signaling. Mouse monoclonal antibodies recognizing PKB, GSK3β, and RhoA were purchased from Transduction Labs. Rabbit polyclonal hemaglutinin (HA), and monoclonal Cdc42 antibodies were obtained from Santa Cruz Biotechnology. Rabbit polyclonal Rac1 antibody was purchased from Cytoskeleton, Inc. We generated a β-parvin (ParvB) rabbit polyclonal serum and affinity-purified these antibodies over an immobilized GST-ParvB column. Mouse monoclonal GAPDH was purchased from Ambion, Inc. Proteins were visualized with an enhanced chemiluminescence (ECL) detection reagent (Amersham Pharmacia Biotech) and quantified by densitometry.

Adenovirus-Mediated Expression of ILK Variants in Primary Cardiomyocytes

Human fetal cardiomyocytes (HFCM) (gestational age 15-20 weeks) were obtained under an Institutional Review Board-approved protocol and cultured to approximately 50% confluency (day 3-4 post-plating) in preparation for adenovirally-mediated infection of ILK constructs, as previously described. Replication-deficient serotype 5 adenovirus encoding either the human wild-type ILK gene (Ad-ILK$^{WT}$), kinase inactive (Ad-ILK$^{R211A}$) or empty virus constructs previously shown to modulate ILK expression and activity in L6 myoblasts, were used for infection of HFCM. HFCM were infected at 37° C. at multiplicity of infection of 2. KP392 is a small molecule inhibitor of ILK which was used to probe the effects of ILK on the profile of Rho family GTPase activation.

Human Ventricular Samples

Human right ventricular samples were derived from two patients with congenital outflow tract obstruction undergoing surgical repair, and left ventricular myocardial samples from five patients with hypertrophic obstructive cardiomyopathy (HOCM) presenting with discrete subaortic muscular obstruction. Control human ventricular tissue was acquired from structurally normal hearts (n=5) which were not used for cardiac transplantation. All human tissue samples were snap-frozen in liquid nitrogen at the time of procurement. All human tissue was acquired following protocol review and approval by the appropriate Research Ethics Board, and the protocols were conducted in accordance with the Tri Council Policy Statement for Research Involving Humans.

Figure 1:
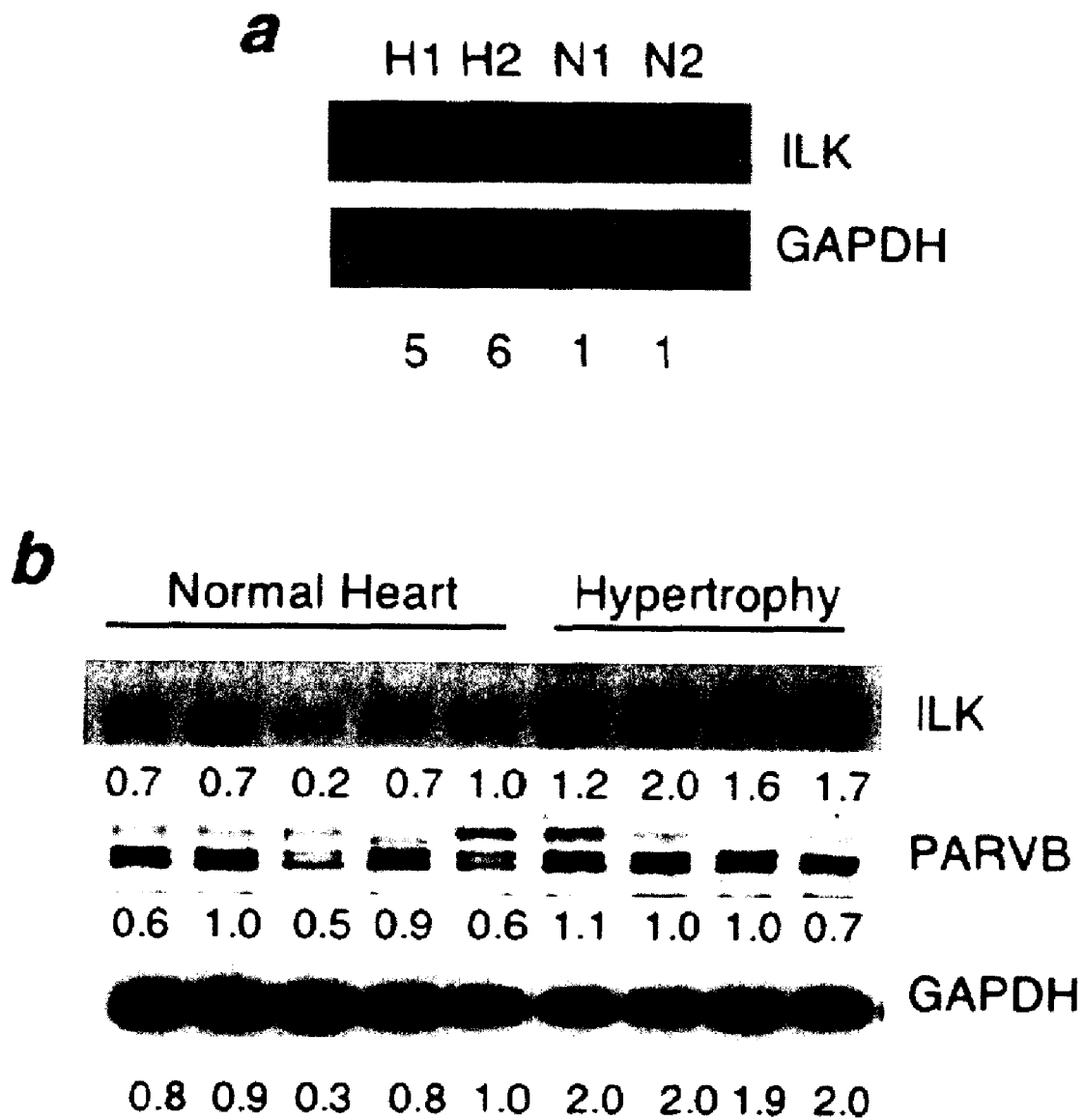
FIG. 1: ILK expression in normal and hypertrophied human ventricles: a, Ventricular lysates from patients with congenital outflow tract obstruction (H1, H2), exhibiting severe hypertrophic valvular heart disease, and from (non-hypertrophic) normal human fetal (19 weeks old) ventricle (N1, N2), were immunoblotted for levels of ILK protein, with GAPDH as loading control. Ratios indicate ILK protein levels normalized to GAPDH. b, Ventricular lysates from hypertrophic (HOCM) and normal (non-hypertrophied) human hearts were analyzed by western blotting for levels of ILK and ParvB. GAPDH was the loading control.

ILK protein levels are elevated in cases of human cardiac hypertrophy. In order to test for the participation of ILK in hypertrophic heart disease in vivo, we examined ILK expression in human ventricular tissue samples from patients with and without clinically evident hypertrophy. Ventricular samples were acquired from two patients in the first year of life with ventricular hypertrophy secondary to congenital outflow tract obstruction; control ventricular tissue was derived from structurally normal 19 week human fetal hearts (n=2), and examined in parallel for levels of ILK expression. Ventricular tissue from these hearts exhibited a 5-6 fold increases in ILK protein levels over control levels (FIG. 1a).

We then investigated whether ILK protein expression was elevated in hypertrophy caused by left ventricular outflow tract obstruction (LVOT), since clinical hypertrophic heart disease more commonly affects the LV. Surgical specimens were acquired from the LVOT in adult patients (n=4) with hypertrophic obstructive cardiomyopathy (HOCM) exhibiting resting LVOT gradients>50 mmHg. Control ventricular tissue was obtained from structurally normal hearts (n=5) at the time of multi-organ transplantation procurement. Myocardial samples from HOCM patients exhibited a ~2 fold increase in ILK protein levels relative to control hearts (FIG. 1b). Thus, the cases of clinical hypertrophy all demonstrate elevation of ILK protein, suggesting this is a critical molecular response to increased cardiac loading and the development of hypertrophy.

ILK has been shown to activate Rho family GTPases, which have also been causally implicated in experimental hypertrophy. We therefore assayed the ventricular tissues directly for activation of RhoA, Cdc42 and Rac1 GTPases, using specific affinity binding assays that distinguish the GDP-bound (inactive) and GTP-bound (active) states of each. Strikingly, there was a ~2-fold and 10-fold increase in Rac1 GTP loading in the hypertrophic ventricular samples from patients with acquired and congenital and outflow tract obstruction, respectively (FIGS. 2ab). Cdc42 activation of ~2-fold was also evident in both acquired and congenital hypertrophic lesions. Conversely, the levels of GTP-bound RhoA were unchanged between the control and hypertrophied ventricles. These results indicate selective activation of Rac1, and to a lesser extent, Cdc42, coincident with increased ILK protein levels, in human ventricular hypertrophy induced in both left and right ventricles by obstructive hemodynamic loading.

Figure 3:
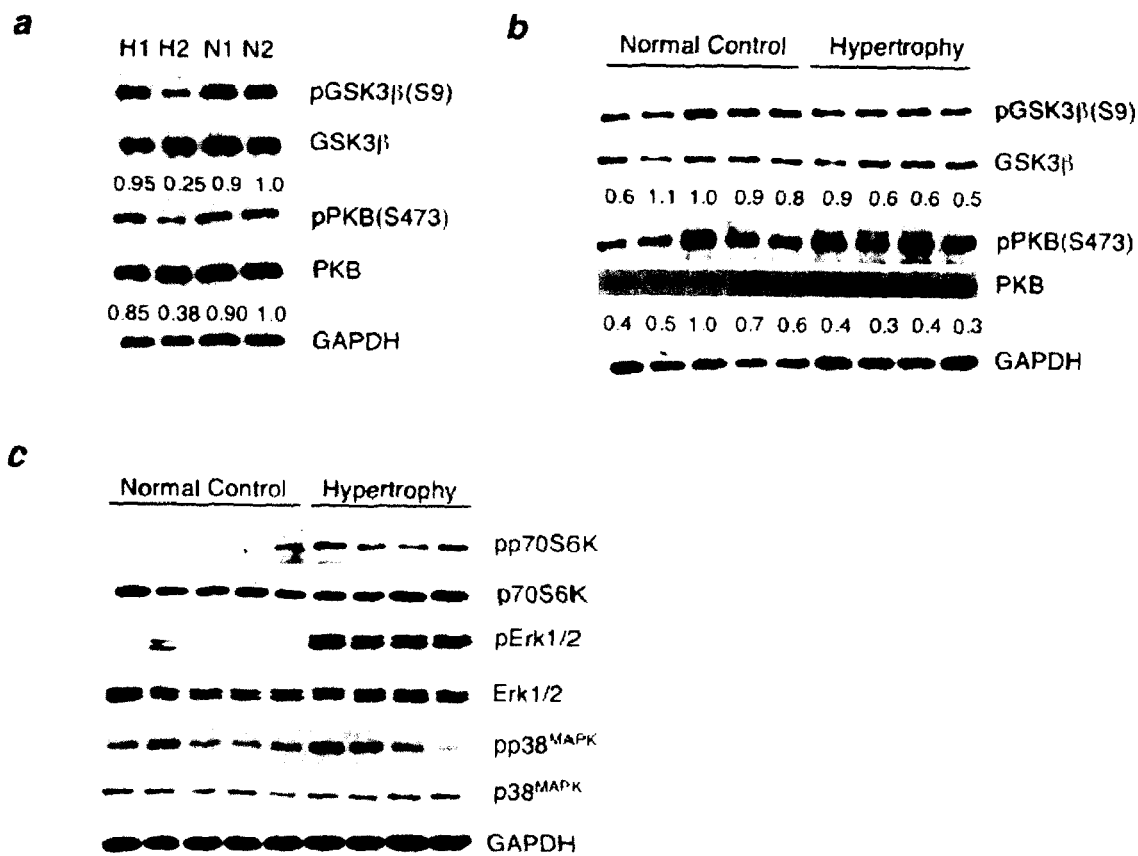
FIG. 3: Phosphorylation of GSK3β, PKB, and MAP kinase in human heart tissue: a, Ventricular lysates labeled N1, N2, H1 and H2 were as in FIGS. 1 and 2, above. b and c, Ventricular lysates from normal and hypertrophic human adult hearts, were as in FIGS. 1 and 2. Lysates were resolved by SDS-PAGE and analyzed by western blotting for levels of the indicated total and phosphorylated proteins.

As the pro-hypertrophic kinases, Akt/PKB, GSK3β, and ERK1/2, are known targets of ILK, we ascertained whether these proteins were also elevated in the cases of human hypertrophy. Western blotting for total protein indicated equivalent levels of GSK3β and ERK1/2 in the hypertrophied hearts, and an increase in PKB (FIG. 3). We tested the hypertrophic hearts for concordant increases in the phosphorylation state of known kinase targets of ILK that have also been implicated in the promotion of cardiac hypertrophy. Surprisingly, the phosphorylation state of the classical hypertrophic signaling targets, Akt/PKB and GSK3β, was not increased above control levels in any of the samples from the human hypertrophic ventricles (FIGS. 3ab), despite the increased ILK protein levels in these samples. This result suggests that a putative ILK-Rac1 hypertrophic pathway is separable from ILK signaling through PKB/Akt and GSK3β. ERK1/2, p38MAPK8, and p70S6K, are kinases downstream of ILK which have also been implicated in promotion of experimental cardiac hypertrophy in vivo. In contrast to Akt/PKB and GSK3β, ERK1/2 and p70S6K were strongly phosphorylated in ventricular lysates in the setting of LVOT obstruction (FIG. 3c), indicative of an activation profile of ILK kinase targets induced during human hypertrophy which appears to exhibit a degree of selectivity.

Cardiac-specific expression of activated ILK in transgenic mice induces hypertrophy. The selective elevation of ILK levels in clinical cases of cardiac hypertrophy prompted us to ask whether increased ILK expression is causative of cardiac hypertrophy. To directly test hypertrophic responses to ILK in vivo, we derived independent lines of transgenic mice harboring different ILK transgenes, expressed under control of the cardiac specific –MHC promoter. As discussed above, ILK is a multifunctional protein24, thus our strategy was to generate lines expressing ILK variants that would allow us to differentiate kinase-dependent and -independent ILK functions in the heart. Toward this end, lines expressing: 1) constitutively activated, ILK$^{S343D}$, 2) wildtype, ILK TgWT, and 3) kinase-inactive ILK, ILK$^{R211A}$, were derived. Southern blot analyses of genomic DNA identified mice carrying the ILK$^{S343D}$ transgene (FIG. 4a), and RT-PCR analysis indicated cardiac-specific expression of ILK$^{S343D}$ (FIG. 4b). Densitometric analysis of western blots indicated that transgenic ILK$^{S343D}$ protein levels were approximately 3-fold higher in transgenic animals, relative to non-transgenic littermates (FIG. 4c), and comparable to the increased levels seen in the clinical hypertrophic samples. Importantly, immune complex kinase assays confirmed that ILK activity in transgenic heart tissue measured in the ILK$^{S343D}$ genotype was elevated relative to non-transgenic controls, in parallel with ILK protein levels (FIG. 4d). Similar analyses confirmed generation of ILK$^{WT}$ and ILK$^{R211A}$ transgenic lines (not shown).

Hearts from ILK$^{S343D}$ Tg mice exhibited concentric hypertrophy, evidenced by gross enlargement and increased heart weight:body weight ratio (FIG. 5a; Supplementary Table 1), and echocardiographic measurements showing significant LV wall thickening, compared to NTg mice (Supplementary Table 2). We observed an approximately 29% increase (p<0.001) in cardiomyocyte area in ILK$^{S343D}$ Tg animals, as assessed in laminin-stained sections of LV (FIG. 5b), which is sufficient to account for the observed cardiac enlargement in ILK$^{S343D}$ Tg mice, suggesting ILK activity regulates cardiomyocyte size, rather than proliferation. There was no conspicuous increase in collagen deposition in the ILK$^{S343D}$ Tg hearts, as assessed histologically using Masson's trichrome (FIG. 5b) or picrosirius red staining. The ILK$^{S343D}$ Tg mice appeared healthy, with no evidence of peripheral edema or cardiac failure, as there were no ILK-induced differences in absolute or body weight-indexed lung and liver weights (Supplementary Table 1). These data indicate that expression of activated ILK in the heart induces hypertrophy without the development of cardiac failure.

TABLE 1

Supplemental. Heart, lung, liver weights of ILK$^{S343D}$ transgenic mice

|  | Transgenic | Non-Transgenic | % Increase | p-value |
|---|---|---|---|---|
| 7 weeks | | | | |
| No. of mice | n = 7 | n = 7 | | |
| Body weight (g) | 21 ± 4.5 | 22 ± 2.7 | −4.5 | NS |
| Heart weight (mg) | 144 ± 7.8 | 126 ± 7.9 | 14 | <0.05 |
| Lung weight (mg) | 173 ± 22 | 183 ± 16 | −5.5 | NS |
| Liver weight (mg) | 1267 ± 319 | 1275 ± 160 | −0.6 | NS |
| Heart/Body weight (mg/g) | 6.9 ± 1.3 | 5.7 ± 0.7 | 21 | <0.05 |
| Lung/Body weight (mg/g) | 8.2 ± 1.6 | 8.3 ± 0.9 | 0.0 | NS |
| Liver/Body weight (mg/g) | 60 ± 5.6 | 58 ± 23 | 3.0 | NS |

TABLE 1-continued

Supplemental. Heart, lung, liver weights of ILK$^{S343D}$ transgenic mice

|  | Transgenic | Non-Transgenic | % Increase | p-value |
|---|---|---|---|---|
| 15 months | | | | |
| No. of mice | n = 7 | n = 6 | | |
| Body weight (g) | 45 ± 3.5 | 41 ± 4.3 | 9.8 | NS |
| Heart weight (mg) | 233 ± 22 | 167 ± 19 | 40 | <0.001 |
| Lung weight (mg) | 203 ± 25 | 197 ± 34 | 3.0 | NS |
| Liver weight (mg) | 1602 ± 410 | 1510 ± 324 | 6.0 | NS |
| Heart/Body weight (mg/g) | 5.2 ± 0.5 | 4.1 ± 0.5 | 27 | <0.05 |
| Lung/Body weight (mg/g) | 4.5 ± 0.8 | 4.8 ± 0.97 | −4.0 | NS |
| Liver/Body weight (mg/g) | 36 ± 6.8 | 37 ± 6.4 | −2.7 | NS |

To further characterize ILK$^{S343D}$-induced hypertrophy, M-mode echocardiography was performed at 3, 5 and 15 months of age in male ILK Tg$^{S343D}$ and NTg mice. At all time points, ILK$^{S343D}$ Tg mice exhibited significant increases in LV mass as well as LV free wall dimensions at end-systole and end-diastole (FIG. 5c, Supplementary Table 2). Cardiac function, however, was preserved as assessed by measures of LV wall shortening fraction and the velocity of LV circumferential fiber shortening (Vcf). Invasive hemodynamic measurements performed at 3 months revealed no significant differences in measures of contractility (dp/dtmax), lusitrophy (dp/dtmin), afterload or heart rate in ILK TgS343D mice relative to NTg controls (Supplementary Table 3), indicating that ILK-induced hypertrophy does not alter cardiac function. Thus, based on the observed lack of cardiac failure and normal hemodynamic function, the cardiac phenotype associated with ILK$^{S343D}$ expression is indicative of a compensated form of hypertrophy.

TABLE 2

Supplemental. Echocardiography of ILK$^{S343D}$ transgenic mice

|  | Transgenic | | Non-transgenic | |
|---|---|---|---|---|
|  | 3 months | 15 months | 3 months | 15 months |
| No. of mice | n = 8 | n = 7 | n = 7 | n = 6 |
| LVEDAW (mm) | 0.93 ± 0.12* | 1.21 ± 0.21* | 0.75 ± 0.11 | 0.99 ± 0.12 |
| LVEDD (mm) | 3.97 ± 0.34 | 4.77 ± 0.24* | 4.04 ± 0.68 | 4.49 ± 0.16 |
| LVEDPW (mm) | 0.85 ± 0.21* | 0.96 ± 0.13* | 0.64 ± 0.027 | 0.83 ± 0.12 |
| LVESAW (mm) | 1.36 ± 0.20* | 1.66 ± 0.22* | 1.86 ± 0.12 | 1.39 ± 0.15 |
| LVESD (mm) | 2.65 ± 0.41 | 3.53 ± 0.24* | 2.68 ± 0.54 | 3.25 ± 0.27 |
| LVESPW (mm) | 1.18 ± 0.25 | 1.30 ± 0.19 | 0.98 ± 0.23 | 1.09 ± 0.30 |
| Vcf (mm/s) | 18.76 ± 1.97 | 21.15 ± 4.58 | 18.58 ± 3.95 | 20.29 ± 3.96 |
| % FS | 33.44 ± 6.07 | 28.32 ± 4.17 | 33.98 ± 9.61 | 27.8 ± 4.71 |
| Stroke Volume (mm$^3$) | 2.37 ± 0.93 | 2.57 ± 1.19 | 2.86 ± 1.98 | 2.09 ± 1.0 |
| LV Mass (mg$^3$) | 136 ± 13** | 239 ± 51** | 104 ± 13 | 170 ± 22 |

*p < 0.05,
**p < 0.001, vs NTg mice.
LVEDAW, LV end-diastolic anterior wall thickness;
LVEDD, LV end-diastolic dimension;
LVEDPW, LV end-diastolic posterior wall thickness;
LVESAW, LV end-systolic anterior wall thickness;
LVESD, LV end-systolic dimension;
LVESPW, LV end-systolic posterior wall thickness;
Vcf, Velocity of circumferential fiber shortening;
% FS, % fractional shortening.

TABLE 3

Supplemental. Hemodynamic function in ILK$^{S343D}$ transgenic mice

| | ILK$^{S343D}$ | Non-Transgenic | p-value |
|---|---|---|---|
| No. of mice | n = 9 | n = 10 | |
| Heart rate (bpm) | 256 ± 14 | 246 ± 20 | NS |
| ABPs (mmHg) | 93 ± 2.9 | 90 ± 1.6 | NS |
| ABPd (mmHg) | 62 ± 4.3 | 58 ± 2.4 | NS |
| LVSP (mmHg) | 92 ± 1.7 | 95 ± 2.6 | NS |
| LVDP (mmHg) | 16 ± 2.2 | 16 ± 1.8 | NS |
| RVSP (mmHg) | 27 ± 0.9 | 26 ± 0.8 | NS |
| RVDP (mmHg) | 2.8 ± 0.7 | 2.9 ± 0.6 | NS |
| dp/dt+ (mmHg/sec) | 4717 ± 190 | 4100 ± 322 | NS |
| dp/dt− (mmHg/sec) | 3342 ± 347 | 3649 ± 201 | NS | dp/dt+ (mmHg/sec), maximal rate of isovolumic LV pressure change;
dp/dt− (mmHg/sec), minimum rate of isovolumic LV pressure change;
ABPs, aorotic systolic blood pressure;
ABPd, aorotic diastolic blood pressure;
LVSP, left ventricular systolic pressure;
LVDP, left ventricular diastolic pressure;
RVSP, right ventricular systolic pressure;
RVDP, right ventricular diastolic pressure.

Induction of cardiac hypertrophy is dependent on the activity of ILK. Our results, showing hypertrophic induction by the activated ILK allele, as well as activity-dependent induction of MAPK, ERK1/2, and p70S6K phosphorylation, suggested that ILK-induced hypertrophy is dependent on ILK activity. In order to test this idea directly, we compared the hypertrophic status of hearts from transgenic mice expressing ILK$^{WT}$, with hearts from ILK$^{R211A}$ transgenic mice. ILK$^{WT}$ hearts exhibited a hypertrophic phenotype which closely mimicked that of the ILK343D mutant, as evident by the significant (p<0.001) increase in HW:BW (Supplementary Table 4) and LV mass measured by echocardiography (p<0.001) in comparison to NTg littermate controls (Supplementary Table 5). Additionally, transgenic mice with cardiac-restricted expression of the kinase-inactive ILK construct (ILK$^{R211A}$) did not develop cardiac hypertrophy, as assessed by echocardiography at 4 months of age (Supplementary Table 6). The finding that cardiac over-expression of kinase-deficient ILK did not exhibit evidence of cardiac dysfunction suggests that the structural role of ILK is sufficient for maintenance of baseline ventricular function, whereas kinase activity is required for hypertrophic remodeling. The G-protein activation profile correlated with the cardiac phenotypic findings, featuring selective activation of Rac1 and Cdc42 in the ILK$^{WT}$ (FIG. 6ab) and ILK$^{S343D}$ Tg (Supplementary FIG. 1) genotypes, both of which develop hypertrophy, in comparison to the kinase-inactive ILK$^{R211A}$, which exhibits a cardiac phenotype indistinguishable from control.

TABLE 4

Supplemental. Heart, lung, liver weights of ILK$^{WT}$ and ILK$^{R211A}$ transgenic mice

| | Transgenic | Non-Transgenic | % Increase | p-value |
|---|---|---|---|---|
| ILK$^{R211A}$ (4 months) | | | | |
| No. of mice | n = 10 | n = 5 | | |
| Body weight (g) | 24 ± 2.6 | 23 ± 3.2 | 4.3 | NS |
| Heart weight (mg) | 112 ± 17 | 106 ± 17 | 5.7 | NS |
| Lung weight (mg) | 220 ± 79 | 219 ± 63 | 0.5 | NS |
| Liver weight (mg) | 1277 ± 199 | 1219 ± 119 | 4.8 | NS |
| Heart/Body weight (mg/g) | 4.7 ± 0.5 | 4.6 ± 0.8 | 2.1 | NS |
| Lung/Body weight (mg/g) | 9.2 ± 2.4 | 9.5 ± 3.5 | −3.2 | NS |
| Liver/Body weight (mg/g) | 53 ± 8.9 | 53 ± 11 | 0 | NS |
| ILK$^{WT}$ (4 weeks) | | | | |
| No. of mice | n = 5 | n = 7 | | |
| Body weight (g) | 22 ± 2.1 | 22 ± 4.4 | 0.0 | NS |
| Heart weight (mg) | 126 ± 8.2 | 106 ± 17 | 19 | <0.05 |
| Lung weight (mg) | 238 ± 32 | 236 ± 32 | 0.8 | NS |
| Liver weight (mg) | 1205 ± 190 | 1185 ± 170 | 1.7 | NS |
| Heart/Body weight (mg/g) | 5.7 ± 0.43 | 4.8 ± 0.45 | 19 | <0.001 |
| Lung/Body weight (mg/g) | 11 ± 1.2 | 11 ± 1.6 | 0.0 | NS |
| Liver/Body weight (mg/g) | 55 ± 6.3 | 54 ± 4.9 | 1.9 | NS |

TABLE 5

Supplemental. Echocardiography of ILK$^{WT}$ transgenic mice

| | Transgenic | Non-transgenic |
|---|---|---|
| No. of mice | n = 5 | n = 8 |
| LVEDAW (mm) | 0.94 ± 0.09** | 0.67 ± 0.09 |
| LVEDD (mm) | 3.75 ± 0.27 | 4.05 ± 0.32 |
| LVEDPW (mm) | 0.74 ± 0.11* | 0.53 ± 0.09 |
| LVESAW (mm) | 1.30 ± 0.21* | 0.92 ± 0.13 |
| LVESD (mm) | 2.48 ± 0.52 | 2.97 ± 0.37 |
| LVESPW (mm) | 0.99 ± 0.15* | 0.76 ± 0.08 |
| Vcf (mm/s) | 20.63 ± 4.48 | 18.25 ± 3.60 |
| % FS | 34.41 ± 9.57 | 24.43 ± 6.75 |
| Stroke Volume (mm$^3$) | 2.35 ± 1.35 | 1.33 ± 0.45 |
| LV Mass (mg$^3$) | 112 ± 11** | 83 ± 22 |

*p < 0.05,
**p < 0.001, vs NTg littermates.

TABLE 6

Supplemental. Echocardiography of ILK$^{R211A}$ transgenic mice

| | Transgenic | Non-transgenic |
|---|---|---|
| 3 Weeks old | | |
| No. of mice | n = 7 | n = 5 |
| LVEDAW (mm) | 0.76 ± 0.09 | 0.68 ± 0.11 |
| LVEDD (mm) | 3.60 ± 0.27 | 3.32 ± 0.19 |
| LVEDPW (mm) | 0.66 ± 0.08 | 0.63 ± 0.11 |
| LVESAW (mm) | 1.10 ± 0.05 | 1.05 ± 0.27 |
| LVESD (mm) | 2.31 ± 0.32 | 2.11 ± 0.53 |
| LVESPW (mm) | 1.01 ± 0.11 | 0.99 ± 0.12 |
| Vcf (mm/s) | 18.66 ± 5.20 | 18.81 ± 6.20 |
| % FS | 35.85 ± 6.50 | 36.70 ± 14.0 |
| Stroke volume (mm$^3$) | 2.30 ± 0.55 | 2.20 ± 0.83 |
| LV Mass (mg$^3$) | 78 ± 12 | 74 ± 10 |
| 4 Months old | | |
| No. of mice | n = 7 | n = 3 |
| LVEDAW (mm) | 0.93 ± 0.08 | 0.96 ± 0.07 |
| LVEDD (mm) | 3.58 ± 0.25 | 3.76 ± 0.17 |
| LVEDPW (mm) | 0.75 ± 0.04 | 0.75 ± 0.05 |
| LVESAW (mm) | 1.28 ± 0.12 | 1.36 ± 0.11 |
| LVESD (mm) | 2.34 ± 0.30 | 2.47 ± 0.23 |
| LVESPW (mm) | 1.10 ± 0.11 | 1.14 ± 0.10 |
| Vcf (mm/s) | 19.94 ± 2.10 | 21.64 ± 3.40 |
| % FS | 35.36 ± 4.20 | 34.73 ± 4.20 |

TABLE 6-continued

Supplemental. Echocardiography of ILK$^{R211A}$ transgenic mice

| | Transgenic | Non-transgenic |
|---|---|---|
| Stroke Volume (mm³) | 2.07 ± 0.53 | 2.76 ± 1.0 |
| LV Mass (mg³) | 105 ± 11.5 | 117 ± 11 |

*p < 0.05,
**p < 0.001, vs NTg littermates.

Figure 6:
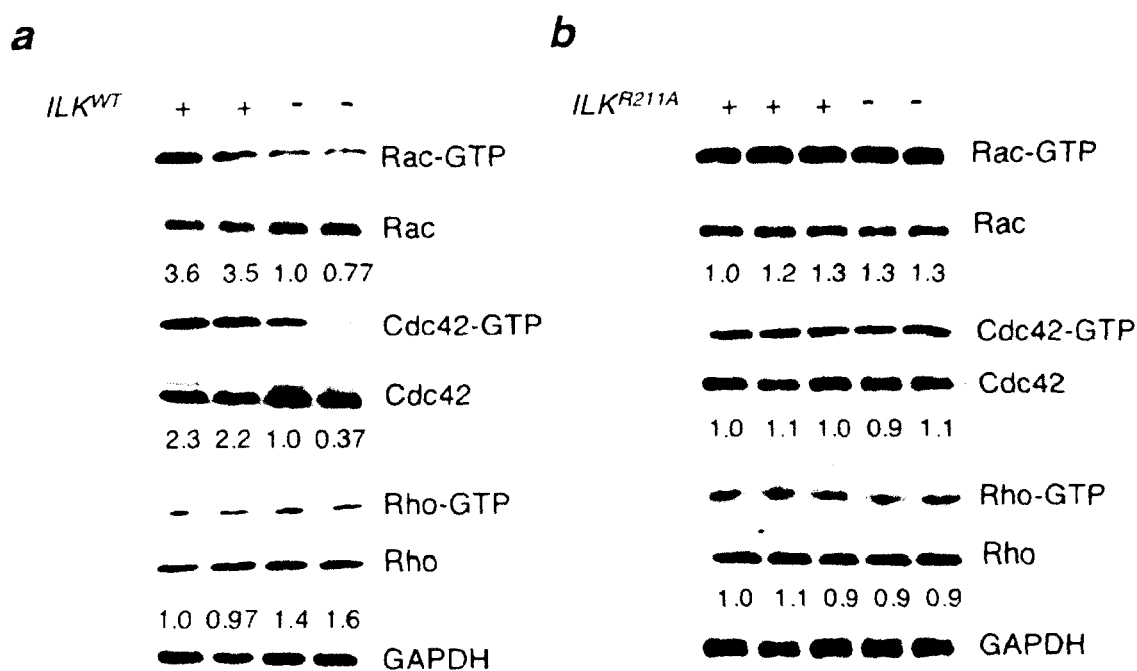
FIG. 6: Selective activation of hypertrophic signaling in ILK$^{WT}$, but not ILK$^{R211A}$ transgenic hearts: Ventricular lysates from a) ILK$^{WT}$ and b) ILK$^{R211A}$ Tg mice were assayed for activation of Rac1, Cdc42 and RhoA, using specific immunoaffinity assays as described in Materials and Methods. In each panel, parallel assays of ventricular lysates from littermate NTg controls are shown. Ventricular lysates from c) ILK$^{WT}$ and d) ILK$^{R211A}$ Tg mice were resolved by SDS-PAGE and analyzed by western blotting for levels of the indicated total and phosphorylated proteins. GAPDH was analyzed in parallel as loading control. Controls were NTg littermates. e. Ventricular lysates form ILK$^{WT}$ and ILK$^{R211A}$ mice were analyzed by western blotting for total ILK, HA tag, and the ILK-associated adaptor, ParvB, as indicated.
Figure 6:
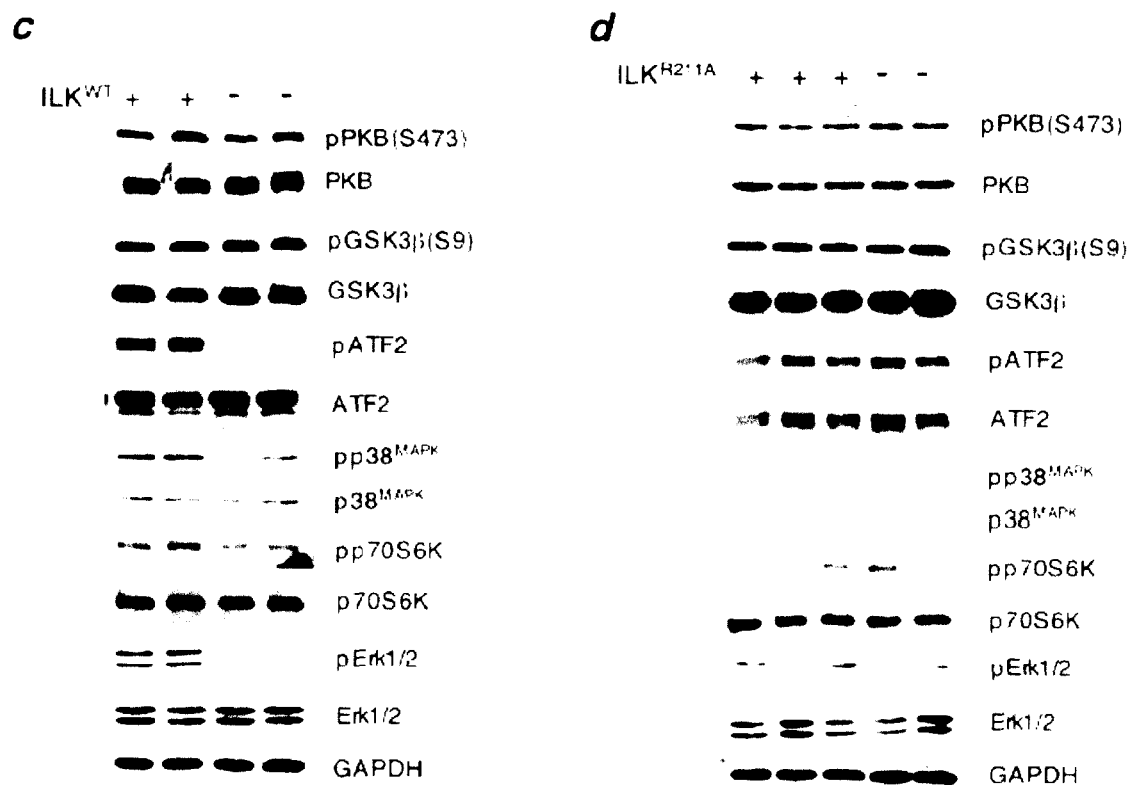
Figure 6:
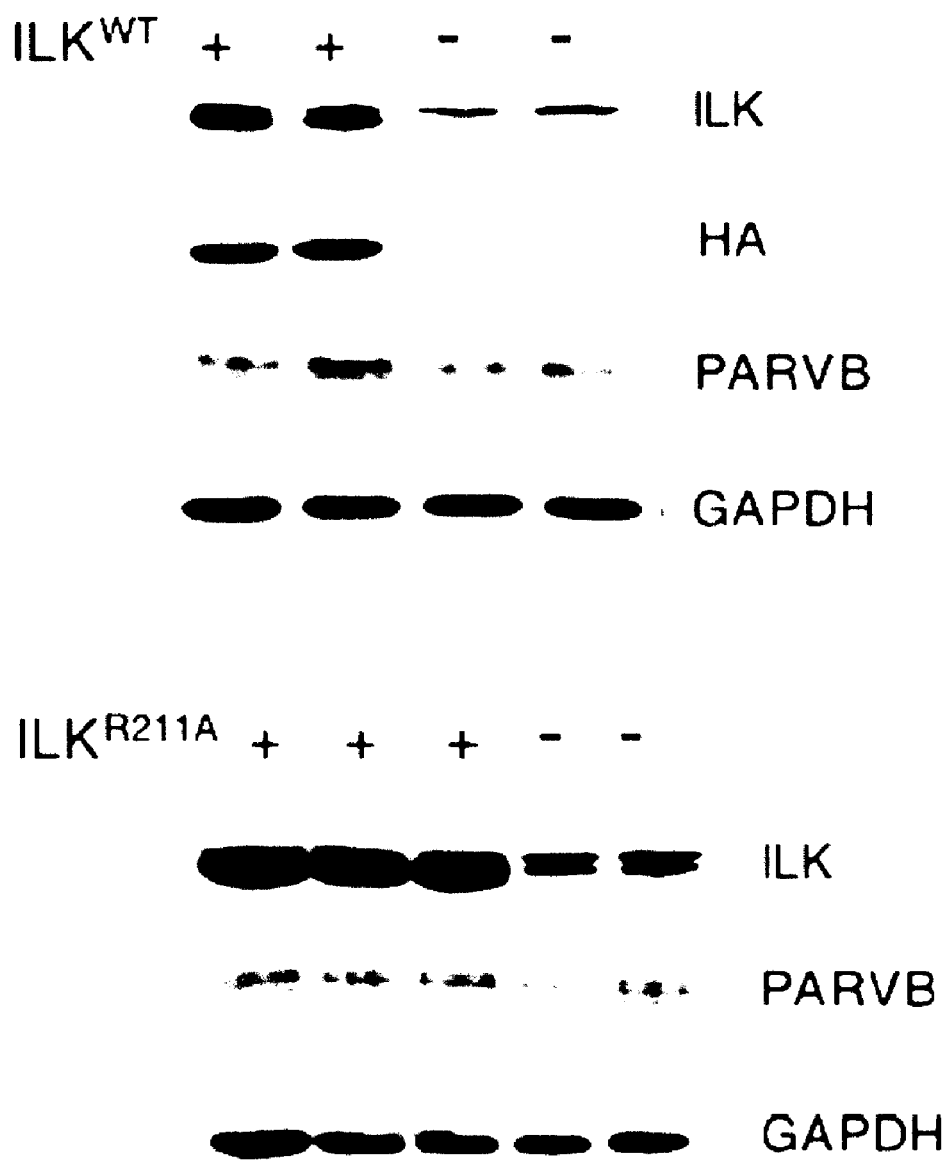

We found that expression of either wild type (FIG. 6cd) or constitutively active (Supplementary FIG. 2) ILK, but not ILK$^{R211A}$, increased phosphorylation of both ERK1/2, and p38MAPK, indicating that activation of these kinases was dependent on ILK catalytic activity. Whereas increased expression of ILK was confirmed in both the ILK$^{WT}$ and ILK$^{R211A}$ genotypes (FIG. 6e), phosphorylation-dependent activation of ILK targets, p70S6K, ERK1/2, p38MAPK, and the p38-dependent transcription factor, ATF2, was only evident in the wild-type over-expressing ventricles (FIG. 6cd). Western blotting confirmed roughly equal expression levels from ILK$^{WT}$ and ILK$^{R211A}$ transgenes (FIG. 6e), suggesting these differences were due to ILK catalytic activity.

Figure 7:
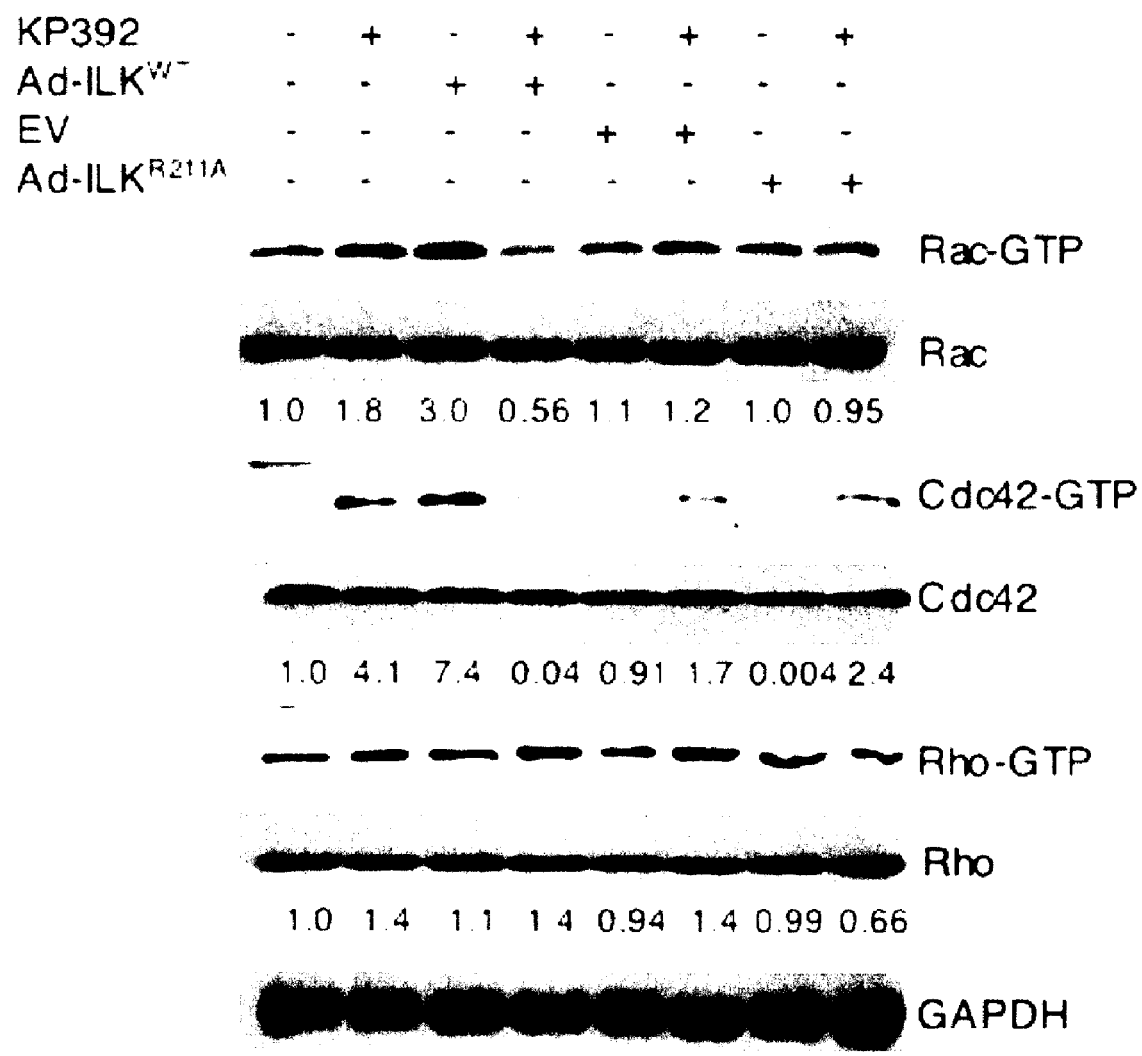
FIG. 7: Selective activation of Rho family GTPases by ILK$^{WT}$, but not ILK$^{R211A}$ in primary human cardiomyocytes: a. Primary human fetal cardiomyocytes were infected with adenoviruses, with or without (EV) ILK$^{WT}$ or ILKR$^{211A}$ cDNA. At 48 hr post-infection, cells sere harvested and lysates assayed for activation of Rho family GTPases. As indicated, cultures were infected in the presence of the small molecule ILK inhibitor, KP-392.

Acute ILK-dependent Rac1 activation in isolated human cardiomyocytes. In order to evaluate the effect of acute ILK up-regulation on GTPase activation, we infected human fetal cardiomyocytes with adenoviruses expressing ILK (Ad-ILK), or an empty virus control. Infection with Ad-ILK stimulated an ~3-fold increase in levels of GTP-bound Rac1 and an ~7-fold increase in GTP-bound Cdc42, 24 hours post-infection (FIG. 7). These stimulations were blocked by treatment of the Ad-ILK infected cells with the small molecule ILK inhibitor, KP-392, suggesting that ILK kinase activity is required for activation of these small GTPases. Infection of the cardiomyocytes with empty adenovirus, carrying no ILK sequences, had no effect on the activation state of Rac1, Cdc42, or RhoA. These results indicate that, as in the transgenic mouse hearts and during human hypertrophy caused by mechanical loading, acute up-regulation of ILK in isolated cardiomyocytes directly activates Rac1 and Cdc42.

Figure 8:
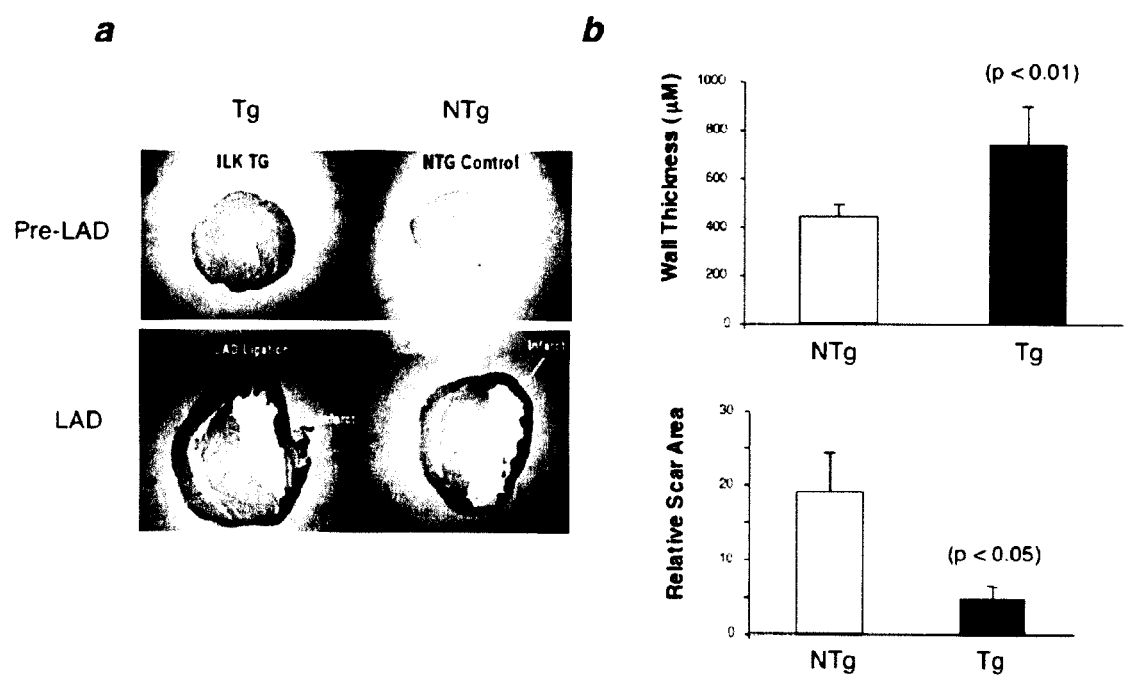
FIG. 8: Cardiac expression of ILK$^{S343D}$ improves post-infarct remodeling: LV infarction was created in 6 month ILK$^{S343D}$ (ILK Tg) and littermate control (NTg) mice by LAD ligation. The ILK TG genotype exhibited a significantly greater LV mass ($p=0.01$) and a reduction in scar area indexed to LV mass ($p=0.047$), as determined by planimetry at 7 days post-infarction. Upper panels, pre LAD ligation; lower panels, post LAD ligation.
Figure 9:
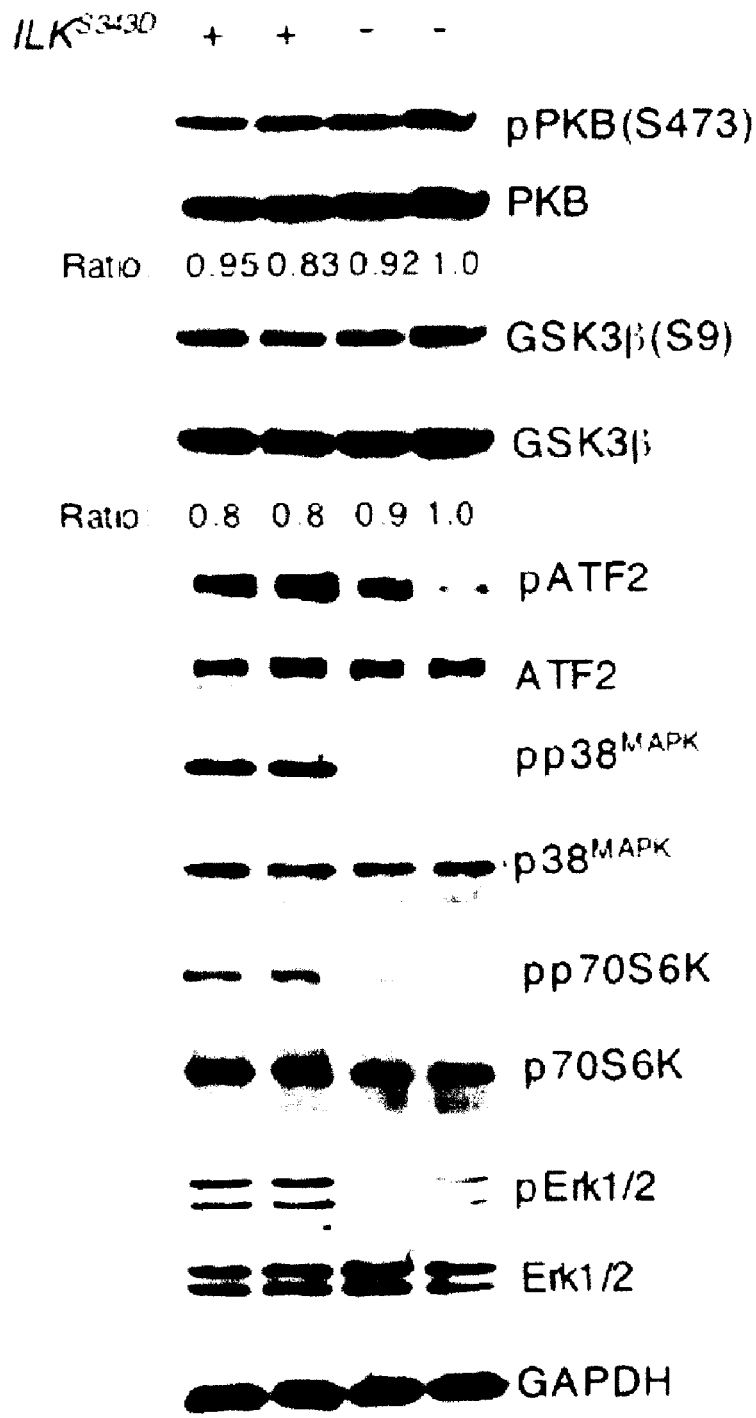
FIG. 9: Activation of hypertrophic signaling in ILK$^{S343D}$ Tg mice: Hearts from two Tg ILK$^{S343D}$ and two NTg littermate controls were extracted and proteins resolved on 10% SDS-PAGE. Western blotting using antibodies against total and phosphorylated forms of the indicated protein kinases was performed to assess the relative activation levels of these pathways. For PKB and GSK3β determinations the ratio of densitometric signals of phosphorylated/total protein were determined for each sample, and are displayed under the panels. GAPDH was used as a loading control.
Figure 10:
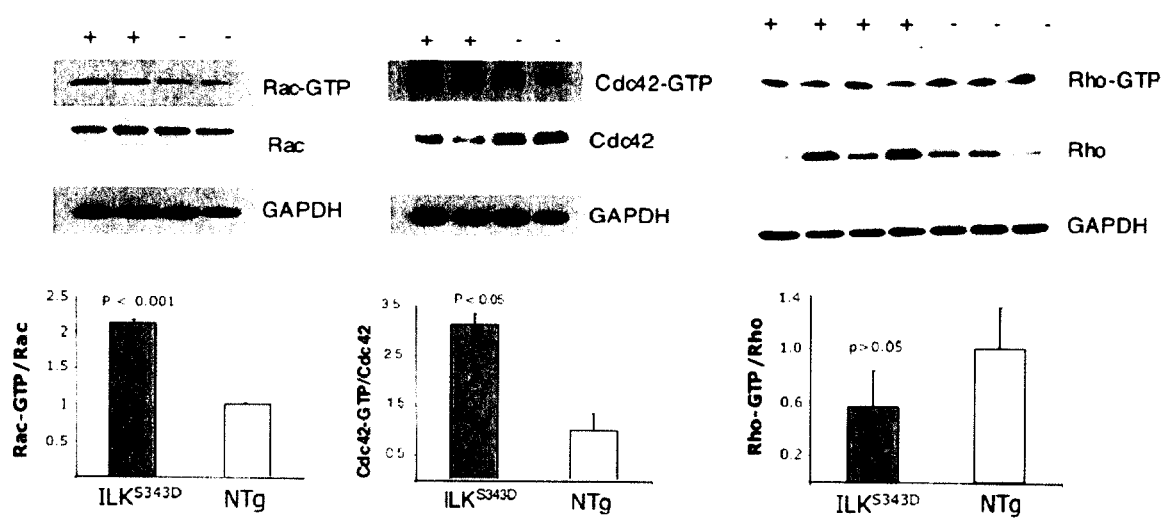
FIG. 10: Selective activation of Rac1 and Cdc42 in ILKS343D Tg mice: Affinity-based precipitation assays were conducted (see Methods) to determine the ratio of GTP-bound (activated) to total: a) Rac1, b) Cdc42 and c) RhoA GTPases in cardiac lysates of ILK$^{S343D}$ Tg and non-Tg littermate mice. Histograms summarize data from 4 hearts of each genotype.
Figure 11:
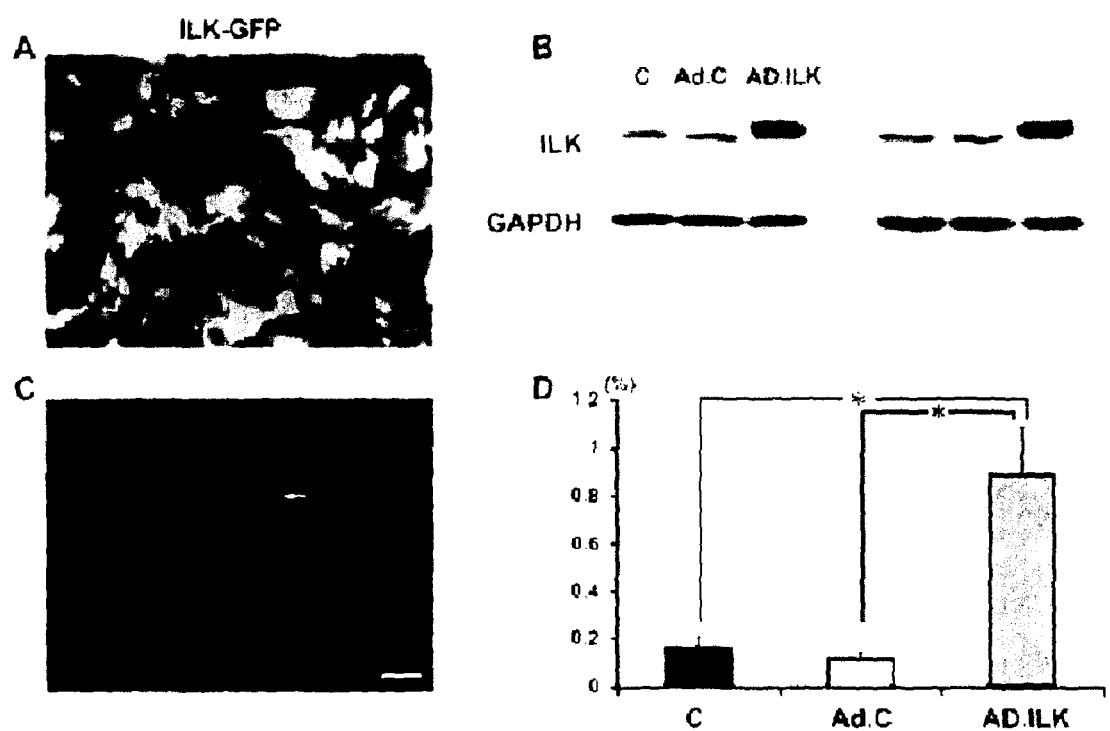
FIG. 11: Adenovirus encoding either the human wild-type human gene linked to GFP (AD.ILK) or empty virus (Ad.C) was used to infect human fetal cardiomyocytes cultured in IMDM supplemented with 10% fetal bovine serum. a Effective gene transfer was confirmed by more than 80% GFP positivity. b ILK infection increased ILK protein expression ~3-fold; the western blots shown are representative of 5 independent experiments. c Cardiac cell cultures labeled with c-Kit (green) and cardiac myosin MF20 (red). Nuclei were stained with DAPI (blue). Scale bar=10 mm. d Cultures infected with ILK yielded a significant ~(*$p=0.001$)~5-fold increase in both the absolute number and the frequency of c-Kit$^{POS}$ cells, which reached ~one cell in 250. Analysis is based on 5 independent experiments. Error bars indicate standard error of the mean.
Figure 12:
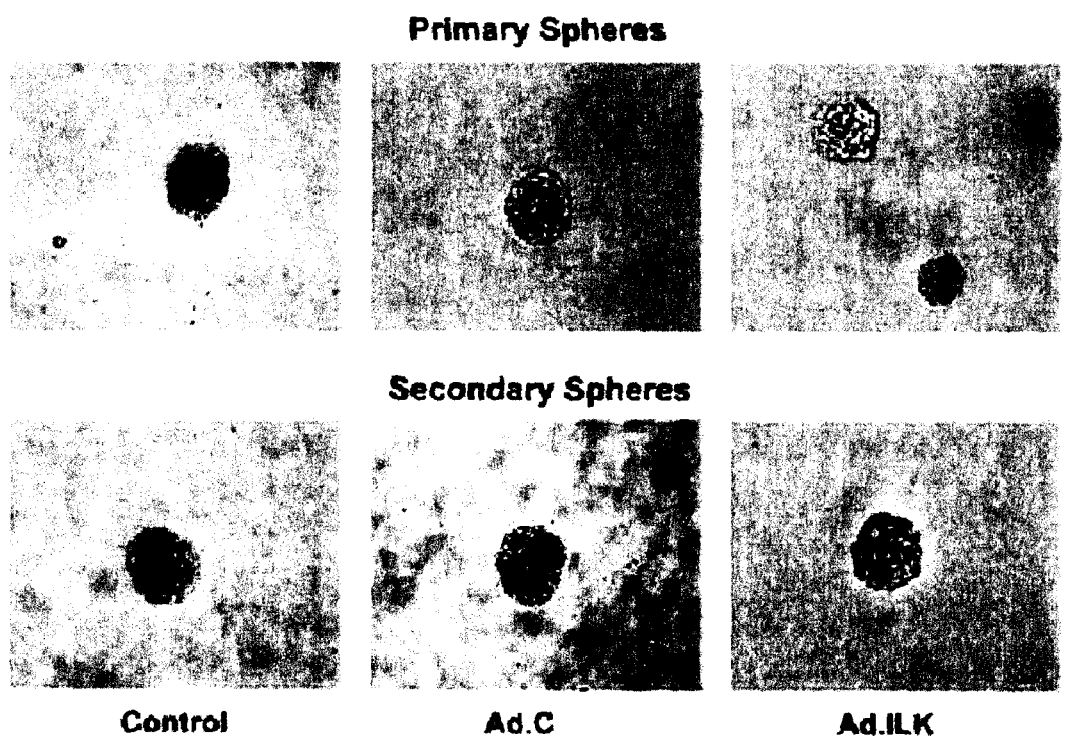
FIG. 12: Primary cardiospheres (CS) were generated from human fetal cardiomyocytes grown in serum-free media supplemented with bFGF and EGF (Methods) and imaged using natural light phase microscopy. Dissociated primary CS comprised of homogeneous phase-bright cells placed in wells containing same media gave rise to secondary CS in approximately 60% of wells.
Figure 13:
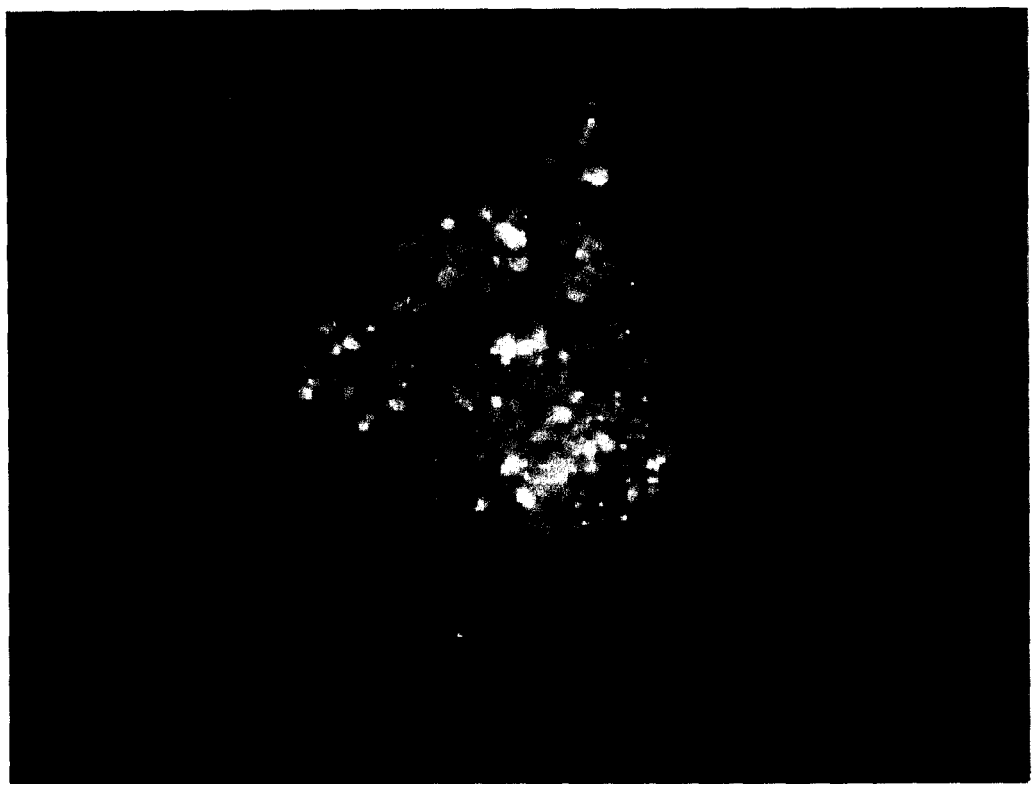
FIG. 13: Cardiospheres were comprised of cells expressing the c-Kit$^{POS}$ surface receptor. Occasional cells at the periphery of the spheres stain for the cardiac marker α-actinin (arrow), suggesting a radial gradient in the differentiation of constituent cells.
Figure 14:
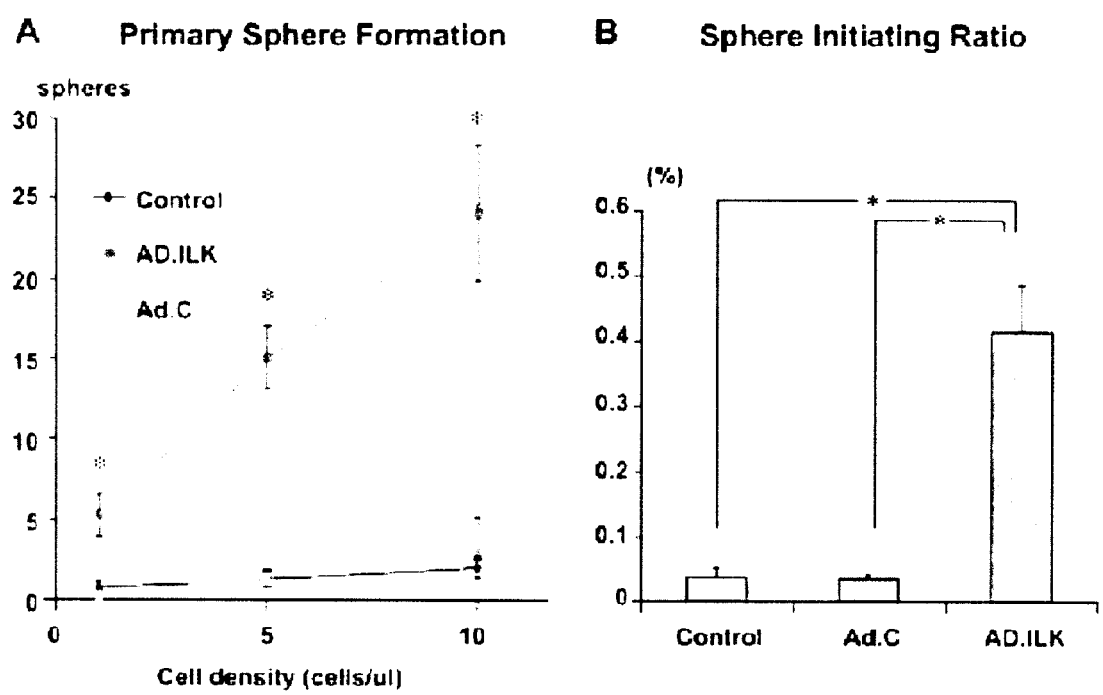
FIG. 14: a Cardiospheres were observed in human fetal cardiac cell cultures. Cardiac cells were infected with adenoviral ILK (Ad.ILK) or empty viral vector (Ad.C) (at 10 pfu/ml), or left untreated (Control). ILK infection resulted in significant (*$p<0.01$) increases in the absolute number and frequency of CS at all plating densities tested. b The number of primary sphere initiating cells ratio was significantly higher in ILK-infected cells (*$p=0.002$). Whereas 0.41±0.073% of ILK-infected cells generated spheres, only 0.037±0.014% of control cells and 0.035±0.006% of virus-only cells generated spheres. Analysis is based on 6 independent experiments. Error bars represent standard error of the mean.
Figure 15:
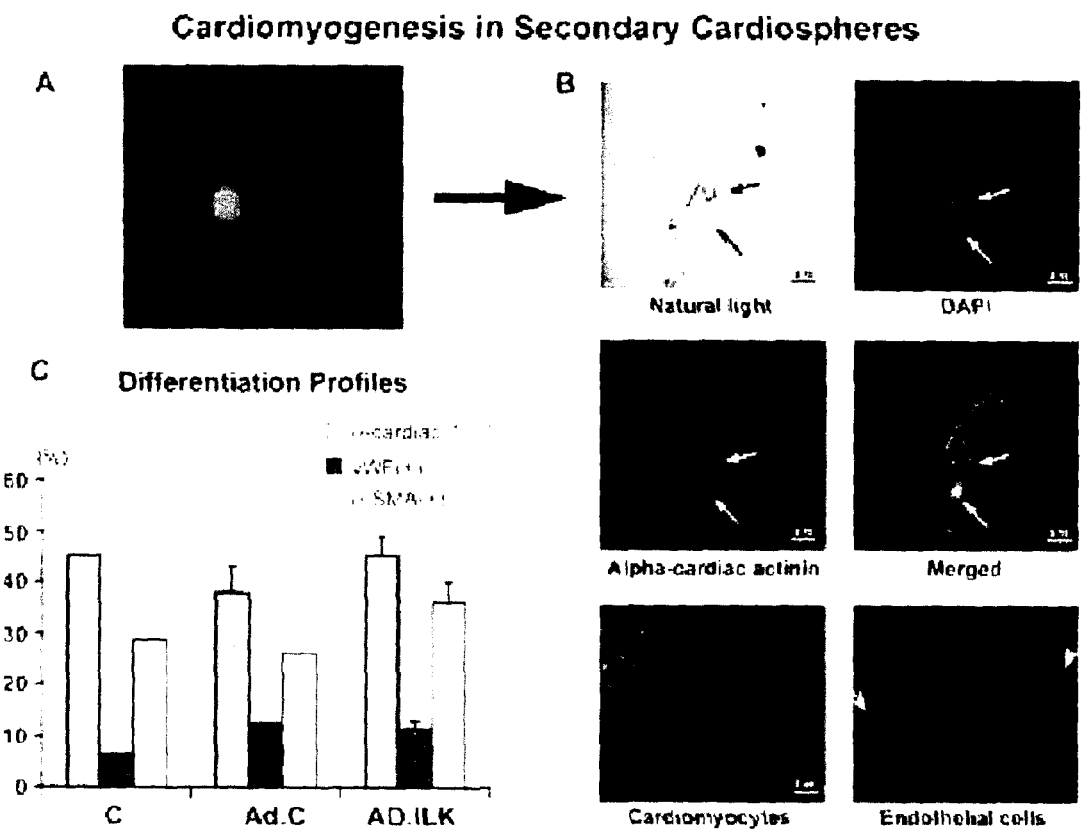
FIG. 15: a Secondary cardiospheres (CS), derived from cells isolated from a dissociated primary CS, shown in upper left panel, contains ILK-infected GFP$_{POS}$ cells. CS were placed in differentiating medium (IMDM+10% FBS) containing the 5-methyltransferase inhibitor, 5-Aza-deoxycytodine (10 μM) for 14 days. b Arrows indicate CS containing cells marked by DAPI staining, which are also positive for the cardiomyocyte-specific marker, α-cardiac actinin. Lower panel (left) shows a higher power view of cells migrating outward from CS, 45-50% of which are cardiomyocytes. Lower panel (right) shows that ~10% of CS-derived cells stain positively (green) for von Willebrands Factor (vWF), indicative of endothelial cell lineage. 35-40% of cells stained positively for α-smooth muscle actin (not shown). c The differentiation profiles were similar among ILK-infected (Ad.ILK), empty virus (AD.C), and control CS. This result indicates the feasibility of manipulating the phenotypic outcome of cardiac progenitor cells, even among ILK-transformed cells.

Genetic ILK over-expression enhances post-infarction remodeling. In order to test for potential cardioprotective effects of ILK, we analyzed LV infarct size in aged 6 month ILK TgS343D and littermate control mice at 7 days post-LAD ligation, based on planimetric scar dimensions measured in six levels of cross-sections of the LV (FIG. 8). The ILK TgS343D genotype exhibited a significantly greater LV mass (p=0.01), a trend towards reduction in absolute LV scar area (p=0.106), and a reduction in scar area indexed to LV mass (p=0.047) (FIG. 8b). Thus, cardiac ILK activation resulted in a post-infarction remodeling phenotype featuring a reactive increase in LV mass.

Recent studies have challenged the traditional thinking that the adult mammalian heart lacks inherent regenerative capacity. Cardiac stem cells (CSCs) derived from bone marrow or niches within the heart have been identified and shown to participate in the regeneration of myocardium in vivo[xii,xiii,xiv]. Tissue-resident cardiac progenitor cells expressing various stem cell markers such as Sca-1, MDR-1, and c-Kit, exhibit the hallmarks of adult stem cells: self-renewal, clonogenicity, and multi-lineage differentiation. However, the population of progenitor cells in the heart is very low, and the inability to expand this population of cells in vitro or in vivo represents a major barrier to therapeutic stem cell applications.

Integrin-linked kinase (ILK) is a multi-functional protein kinase, which coordinates signal transduction by integrins and growth factor receptors, and serves as a nodal regulator of protein kinase cascades important to cell proliferation, differentiation and apoptosis[xv,xvi]. ILK functions as the effector of phosphoinositide-3'-OH kinase (PI3K) signaling following distinct signal inputs from integrins and growth factor receptor tyrosine kinases[xvii,xviii]. ILK also inhibits glycogen synthase kinase-3β (GSK-3β)[xvi,xix], which leads to the nuclear accumulation of β-catenin, which, in turn, leads to the activation of Wnt target genes implicated in the maintenance and symmetric replication of embryonic stem cells, as well as their more tissue- and lineage-restricted progeny. The canonical Wnt/β-catenin signaling pathway has been shown to be important in both embryonic and adult stem cell maintenance and self-renewal in hematopoetic, gastrointestinal and neural tissues[xx,xxi,xxii,xxiii,xxiv,xxv], although this pathway has not been studied in CSCs.

The demonstrable utility of Integrin-linked kinase (ILK) to promote cardiac stem cell proliferation and self renewal is herein set forth. While it was known that Integrin-linked kinase (ILK) is a multi-functional protein kinase, which coordinates signal transduction by integrins and growth factor receptors, and activates Wnt target genes implicated in the maintenance and symmetric replication of embryonic stem cells, the effect of ILK on cardiac stem cells has been heretofore unknown.

Recent evidence suggests that the adult heart contains stem cells, which are capable of self-renewal as well as tissue-specific, multi-lineage differentiation. However, their inherent capacity for self-renewal is limiting to cell replacement applications. We herein demonstrate that a cardiac stem cell population is susceptible to amplification through ILK gain-of-function.

Methods

Primary cultures derived from human fetal cardiac tissue (19-22 weeks gestation) were grown in serum-free media supplemented with growth factors and evaluated for the appearance of cells with the properties of stem cells, including self-renewal and the capacity to differentiate into definitive cardiac myocytes. The effect of ILK was ascertained using adenoviral over-expression of ILK cDNA constructs conveying either gain- or loss-of-function.

Results

Cultures infected with wild type ILK yielded a significant (p=0.001), ~5-fold increase in both the absolute number and the frequency of c-Kit$^{POS}$, myosin$^{NEG}$ cells, which reached ~one cell in 250. Cardiospheres (CS), comprised on morphologically homogeneous, anchorage-independent cells, were reproducibly present at day 7-10, and formed derivative CS in multiple passages. ILK infection of primary cardiac cell cultures resulted in a greater number of primary spheres at each cell density tested, compared with untreated and virus controls (p=0.001). Secondary spheres transferred to differentiation medium consisting of IMDM with 10% FBS and 5-Aza-deoxycytodine (10 uM) generated cells exhibiting biochemical evidence of differentiation into cardiomyocytes, smooth muscle cells and endothelial cells.

Conclusions

This study demonstrates that self-renewing cardiospheres generated from human fetal cardiac cells are comprised of cells exhibiting the properties of stem cells, including the capacity for self-renewal and multilineage differentiation. ILK-transformed stem cells are shown to be equally susceptible to cardiac differentiation, even while exhibiting an increased capacity for proliferation and CS formation. Our results suggest that ILK promotes stem cell amplification and can be applied therapeutically to overcome a major limitation in the field of cardiac regenerative medicine.

Here we show that the overexpression of ILK in human fetal cardiac tissue in vitro increases the population of cardiac stem cells, which exhibit self-renewal and multi-lineage differentiation. Our results suggest that gain-of-function of a gene which promotes stem cell amplification can be applied therapeutically to overcome a major limitation in the field of regenerative medicine.

DETAILED DESCRIPTION OF EXPERIMENTS

Isolation and Cell Culture

Human fetal hearts were harvested during elective pregnancy termination at the gestational ages of 19 to 22 weeks, in accordance with the guidelines of the Institutional Human Research Ethics Board and after obtaining maternal consent.

The hearts were minced and washed using phosphate buffered saline (PBS). Cell isolation was accomplished using 0.2% trypsin and 1.0 mg/mL type II collagenase in a 0.02% glucose PBS solution at 37° C. After dissection, cells were incubated on pre-coated plastic culture dishes (Starstedt) for 2 hours at 37° C. to remove fibroblasts, with IMDM (Gibco) containing Penicillin and Streptomycin and supplemented with 10% fetal bovine serum (Gibco). After incubation, the supernatant was removed and added to pre-coated culture dishes (Starstedt) and placed in a 5% CO2 incubator at 37° C.

Gene Transfer

Cells were cultured to 60-70% confluency in preparation for adenovirally-mediated infection of ILK constructs incorporating green fluorescent protein (GFP), as previously described[xxvi]. Replication-deficient serotype 5 adenovirus encoding either the human wild-type ILK gene (Ad.ILK-GFP) or empty virus constructs (Ad.C) previously shown to modulate ILK expression and activity in L6 myoblasts[xxvii], were used for the infection of cells. Cells were infected at 37° C. at multiplicity of infection of 1.5 in IMDM medium with 10% fetal bovine serum for 24 h. Effective gene transfer was confirmed by more than 80% of GFP positivity.

Western Blot Analysis

Western blot analysis was performed to confirm that the transduction of Ad.ILK in cardiac cell cultures. The cells were washed with PBS and harvested by scraping in lysis buffer. After measurement of protein expression, analyses were performed with polyclonal anti-ILK antibody (Cell Signaling). Proteins were visualized with an enhanced chemiluminescence (ECL) detection reagent (Amersham Pharmacia Biotech) and quantified by densitometry.

Immunocytochemistry and Quantitative Analysis of c-Kit$^{POS}$ Cells

Cells were fixed using methanol at −20° C. for 20 minutes. Cells were then reacted with c-Kit antibody (diluted 1:20; Assay Design Inc.), human monoclonal anti-CD34 (Cymbus Biotechnology), human monoclonal anti-α-smooth muscle actin (1:100; Santa Cruz), human polyclonal anti-Von Willebrand Factor (1:200), myosin monoclonal antibody (MF20 diluted 1:10), or monoclonal anti-α actinin (1:200) from Sigma. Nuclei were stained with DAPI. All slides were analyzed at 20× magnification using a Leica fluorescent microscope with a coupled camera. All analysis was done using Openlab 4.0.2 software. More than ten fields were randomly chosen and photographed, and the total cell number (~5000/dish) was counted manually in a fashion blinded to viral status.

Generation of Primary and Secondary Spheres

Cell viability of cells was confirmed with trypan blue staining prior to plating at densities from 10 cells/µL to 1 cell/µL in 24-well plates. The culture medium was composed of DMEM/F-12 (1:1) including Hepes buffer (5 mM), glucose (0.6%), sodium bicarbonate (3 mM), and glutamine (2 mM), insulin (25 µg/ml), transferrin (100 µg/ml), progesterone (20 nM), putrescine (60 µM), sodium selenite (30 nM), human recombinant EGF (20 ng/ml), and bFGF (20 ng/ml). The number of primary spheres generated in each well was assessed 14 days after plating. Primary spheres were dissociated into single cells consisting of 200-500 cells, which were placed in 96-well plates. The number of secondary spheres was assessed 14 days after replating dissociated cells.

Differentiation Assay

Secondary spheres were transferred to differentiation medium, which was composed of IMDM containing 10% FBS and 10 uM 5-aza-2'-deoxycytodine (5azaD). Cells migrating out from the spheres were analyzed by immunocytochemistry on day 14. Cells were fixed and characterized by staining with the following markers: α-cardiac actinin antibody (diluted 1:100, SIGMA), Von Willebrand factor antibody (diluted 1:200 DAKO), or α-smooth muscle actin antibody (diluted 1:100, Santa Cruz).

Results

ILK Increases the Frequency of c-Kit$^{POS}$ Cells

To determine whether the overexpression of ILK increases the stem cell number in the human heart, fetal hearts of gestational ages 19-22 weeks were acquired during elective pregnancy termination, and the hearts were enzymatically dissociated into single cell suspension. The cells were incubated on pre-coated plastic culture dishes for 2 hours at 37° C. to remove fibroblasts, which were shown to be devoid of c-Kit$^{POS}$ cells. At 2-3 days after isolation and at 60-70% confluency, cells were infected with replication defective adenovirus containing wild type (Ad.ILK), or virus control (Ad.C). Effective gene transfer was confirmed by more than 80% GFP positivity (FIG. 1a) and by ~3-fold increase in ILK protein expression (FIG. 1b) in cell cultures. c-Kit$^{POS}$ cells imaged by fluorescence microscopy were invariably negative for the cardiac myosin markers α-cardiac actinin (FIG. 1c), MF20 and the hematopoetic stem cell marker CD34. Cultures infected with wild type ILK yielded a significant (p=0.001), ~5-fold increase in both the absolute number and the frequency of c-Kit$^{POS}$ cells, which reached ~one cell in 250 (FIG. 1d).

Human Fetal Cardiac Cells Generate Cardiospheres In Vitro

Figure 2:
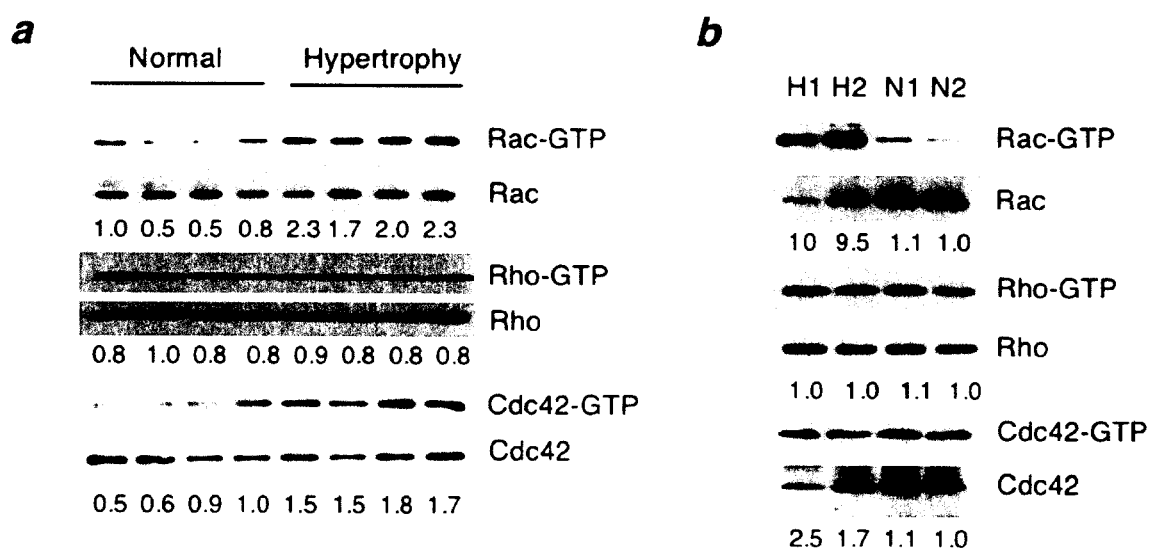
FIG. 2 Rac, Rho and Cdc42 expression in human heart tissue: a, Normal and hypertrophic (HOCM) human ventricular lysates (FIG. 1) were assayed for activation of Rho family GTPases, as indicated. b, Ventricular lysates from the congenital samples (H1, H2) and normal human fetal hearts (19 weeks, FIG. 1) were assayed for Rho family activation. Ratios represent densitometric values of activated/total GTPase signals for Rho, Rac1 and Cdc42.

To determine if primary human fetal cardiac cells generate cardiospheres in vitro, cells were infected with Ad.ILK or control virus and plated in serum-free medium supplemented with 20 ng/ml each of EGF and bFGF at clonal density of a single cell per well in 24-well plates. Primary cardiospheres (CS), comprised on morphologically homogeneous cells, were reproducibly present at day 7-10 (FIG. 2, upper panel). CS were noted to be uniformly free-floating, presumably reflecting anchorage-independence, in distinction to cardiac myocytes which became rapidly adherent to the culture plate surface. Cells from dissociated primary CS were plated at a density corresponding to one sphere (~200-400 cells)/well. Secondary CS, which were morphologically indistinguishable from primary CS, were evident in ~60% of wells at day 14 (FIG. 2, lower panel). CS were shown to be comprised of cells expressing the c-Kit$^{POS}$ surface receptor (FIG. 3). Occasional cells at the periphery of the spheres stained for the cardiac marker α-actinin (arrowhead).

ILK Over-Expression Increases the Rate of CS Formation

ILK infection of primary cardiac cell cultures resulted in a greater number of primary spheres at each cell density tested, compared with untreated and virus controls (FIG. 4a). Among CS generated from ILK-infected cultures, ~80% stained homogeneously for ILK-GFP; ~20% exhibited no evidence of GFP staining; and no spheres were observed which were mosaic for GFP, suggesting origin from a single cell rather than cellular aggregation. The frequency of sphere-initiating cells, as measured by the ratio of sphere number:total cell number, was significantly greater in ILK-overexpressing cultures (FIG. 4b). The frequency of secondary or tertiary spheres generated from primary spheres comprised of Ad.ILK, AD.C or uninfected cells was highly similar (~60% of wells), indicating that while ILK gain-of-function increases the formation of primary spheres, it does not alter their inherent capacity for subsequent self-renewal.

Figure 5:
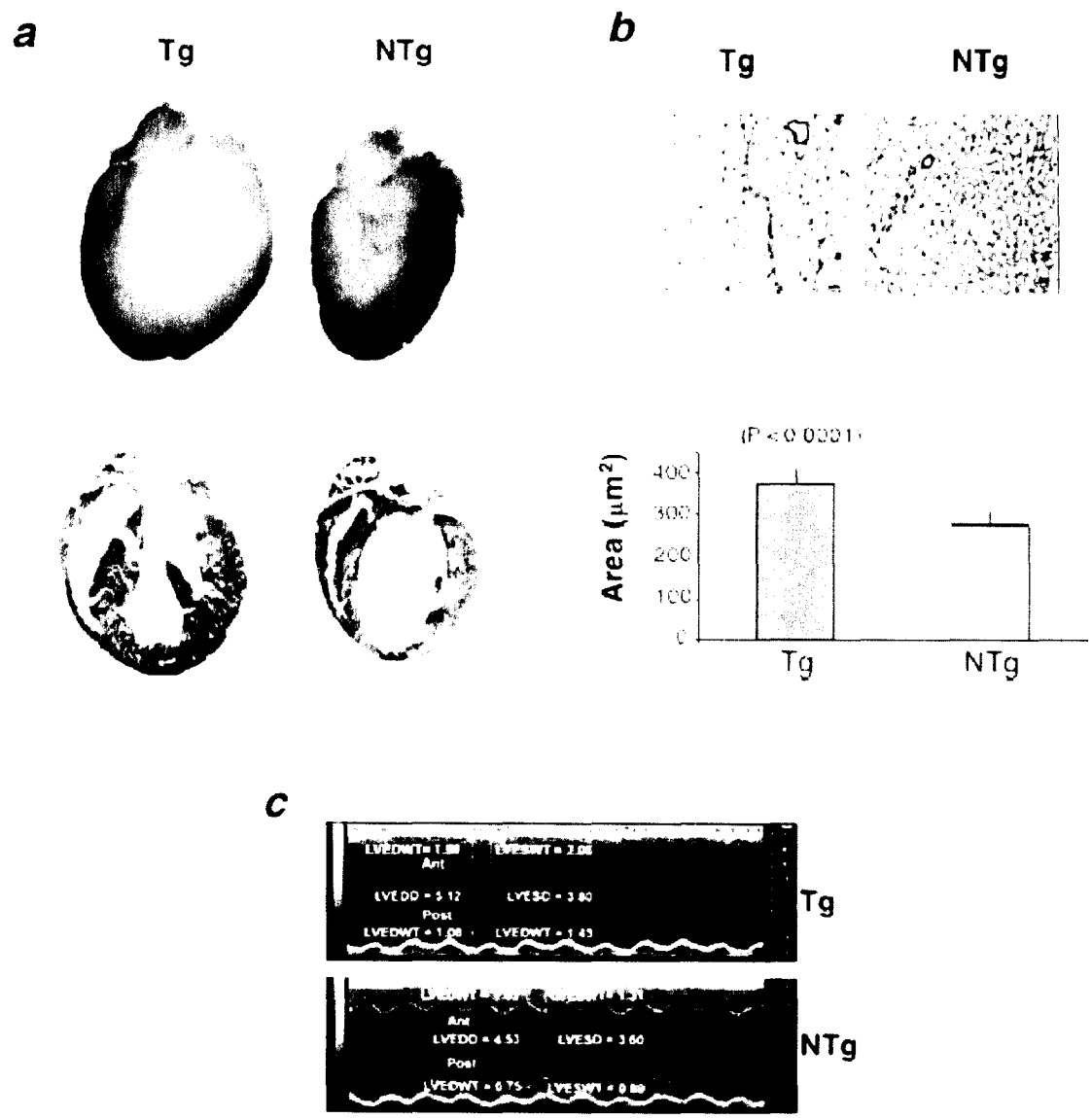
FIG. 5: Increased cardiomyocyte size in ILK$^{S343D}$ Tg mice: a, Gross morphology of hearts from ILK$^{S343D}$ Tg mice and NTg littermates. Enlarged hearts of ILK$^{S343D}$ mice exhibited concentric hypertrophy evident by an approximate 25% increase in heart weight to body weight ratios relative to that in NTg controls (controls for all comparisons are age- and sex-matched littermates, see Table 2B). Histological studies using Masson's trichrome and picrosirius red staining (not shown) indicated no conspicuous increase in collagen in the ILK$^{S343D}$ Tg hearts. b, Mean values of cardiomyocyte areas based on approximately 500 cells per mouse with centrally positional nuclei. This analysis indicated a 20-25% increase in cardiomyocyte area, thereby accounting for the observed increase in LV mass. c, Representative echocardiograms showing details of dimensional measurements. At 15 months, ILK$^{S343D}$ Tg mice exhibited significant increases in LV mass as well as LV cavitary dimensions at end-systole and end-diastole ($p<0.05$), and preserved LV function based on echocardiography (% fractional shortening, Table 1, Supplemental) and invasive hemodynamic measurements (Tables 2 and 3, Supplemental).

Cardiac stem cells are multipotent and have the capacity to differentiate into smooth muscle, cardiac and endothelial cells[xxx,xxxi,xxxii]. Secondary spheres were transferred to differentiation medium consisting of IMDM with 10% FBS and the methyltransferase inhibitor, 5azaD (10 uM). Within 4-5 days spheres became attached to the plate and individual cells migrated from spheres, which exhibited biochemical evidence of differentiation into cardiomyocytes, smooth muscle cells and endothelial cells (FIG. 5). The profile of differentiated cells among ILK-over expressing and control cells was highly similar (FIG. 5, lower left panel), indicating that ILK-induced clonal proliferation of cardiac stem cells does not impair their capacity for multilineage differentiation.

Discussion

These experiments show that primary cultures derived from human fetal cardiac tissue grown in non-serum, growth factor-supplemented media form macroscopic cardiopsheres, analogous to neurospheres containing multipotent neural stem cells[xxviii,xxix]. Cardiospheres (CS) have been previously characterized as lineage-negative (Lin$^{NEG}$) c-Kit$^{POS}$, morphologically homogeneous cells devoid of cardiac markers such as sarcomeric structures, having the capacity for self-renewal, as well as differentiation into functional cardiac myocytes, and to participate in the regeneration of functional myocardium in vivo[xxx,xxxi,xxxii]. Cells comprising CS did not express the hematopoetic stem cell marker CD34, suggesting that CS were derived from a cardiac resident, rather than from a bone marrow-mobilised, cell population[xxxiii].

The evolutionarily conserved canonical Wnt pathway has been implicated in both human and mouse ES cell self-renewal competence[xxii]. The Wnt/β-catenin signaling pathway is required for maintaining proliferation of neuronal progenitors[xxiii], and for haematopoietic stem cell homeostasis[xxv]. ILK negatively modulates of GSK-3β activity and promotes nuclear activation of β-catenin[xxiii,xxxiv,xxxv,xxxvi,xxxvii], and is a candidate kinase activator of Wnt pathway signaling[xvi]. ILK over-expression or constitutive activation promotes cell cycle transit through a signaling pathway comprising the Wnt components GSK-3β and β-catenin, leading to increased expression of cyclin D1[xxxviii], and providing a molecular basis for the inherent proliferation (self-renewal) property of stem cells. Moreover, ILK promotes anchorage-independent survival, which appears to be a generic and poorly understood feature of stem cells, including c-Kit-containing CS isolated from adult rat[xxix] and human hearts[xl].

These experiments validate our initial theory that human fetal cardiac tissue would be enriched for stem cells, which are important during cardiogenesis[xli]. Since it has been reported that cardiac c-Kit positive cells can grow and differentiate into the various cardiac lineages, including cardiomyocytes, smooth muscle and endothelial cells[xiv], c-Kit antibody was used as a marker for cardiac stem cells. The proto-oncogene c-kit encodes a transmembrane tyrosine kinase receptor, and the ligand for c-Kit has been identified to be stem cell factor (SCF)[xlii]. We took advantage of the tendency of cardiac cells to form macroscopic CS when grown on non-adhesive substrata in the presence of growth factor supplementation. Using the capacity to form CS as a readout for stem cell frequency, we tested whether adenoviral ILK overexpression would cause proliferation of CS-forming cells with self-renewal, clonogenic, and multi-differentiation properties.

We have thus demonstrated that self-renewing cardiospheres generated from human fetal cardiac cells are comprised of cells exhibiting the properties of stem cells, including the capacity for self-renewal and multilineage differentiation. This result has been also reported in cardiac cells isolated from adult rodent[xxx], murine[xxxii], and human atrial biopsies[xxxi]. Overexpression of ILK resulted in an ~10-fold increase in the frequency of sphere-initiating cells. Importantly, ILK-transformed stem cells are shown to be equally susceptible to cardiac differentiation, even while exhibiting an increased capacity for proliferation and CS formation.

ILK is positioned to transduce distinct signal inputs from integrins and growth factor receptor tyrosine kinases[xliii,xliv], is an activator of the Wnt pathway[xlv], and promotes anchorage-independent cellular proliferation[xvi,xviii], thus providing a putative molecular basis for the observed amplification effect on the cardiac stem cell population. An ILK-dependent increase in cardiac stem cell frequency is consistent with the finding that vascular endothelial growth factor (VEGF) has been shown to positively regulate hematopoetic stem cell survival[xlvi], since ILK positively regulates VEGF expression through an hypoxia-inducible factor-1α-dependent pathway[xv]. The fact that ILK effect was evident even under conditions of growth factor supplementation supports the rationale of exploiting upregulation the ILK signaling pathway as a novel strategy to promote therapeutically useful expansion of a target stem cell population.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

$^{i}$Nelson W J, Nusse R. Convergence of Wnt, beta-catenin, and cadherin pathways. *Science.* 2004; 303:1483-1487.

[ii] Sato N, Meier L, Skaltsounis L, Greengard P, Brivanlou A H. Maintenance of pluripotency in human and mouse embryonic stem cells through activation of Wnt signaling by a pharmacological GSK-3-specific inhibitor. *Nat Med.* 2004; 10:55-63.

[iii] Choi J H, Hur J. Yoon C H, Kim J H, Lee C S, Youn S W, et al. Augmentation of Therapeutic Angiogenesis Using Genetically Modified Human Endothelial Progenitor Cells with Altered Glycogen Synthase Kinase-3 {beta} Activity. *J Biol Chem.* 2004; 279:49430-49438.

[iv]

[v] Hannigan G E, Leung-Hagesteijn C, Fitz-Gibbon L, Coppolino M G, Radeva G, Filmus J, et al. Regulation of cell adhesion and anchorage-dependent growth by a new beta 1-integrin-linked protein kinase. *Nature.* 1996; 379:91-96.

[vi] Troussard A A, Tan C, Yoganathan N, Dedhar S. Cell-extracellular matrix interactions stimulate the AP-1 transcription factor in an integrin-linked kinase- and glycogen synthase kinase 3-dependent manner. *Mol Cell Biol.* 1999; 19:7420-7427.

[vii] Persad S, Attwell S, Gray V, Delcommenne M, Troussard A, Sanghera J, et al. Inhibition of integrin-linked kinase (ILK) suppresses activation of protein kinase B/Akt and induces cell cycle arrest and apoptosis of PTEN-mutant prostate cancer cells. *Proc Natl Acad Sci USA.* 2000; 97:3207-3212.

[viii] Troussard A A, Mawji N M, Ong C, Mui A, St-Arnaud R, Dedhar S. Conditional knock-out of integrin-linked kinase demonstrates an essential role in protein kinase B/Akt activation. *J Biol Chem.* 2003; 278:22374-22378.

[ix] Coles J G, Takahashi M, Grant D, Dai X, Du C, Boscarino C, et al. Cardioprotective stress response in the human fetal heart. *JTCVS.* 2004. In Press.

[x] Konstantinov I E, Coles J G, Boscarino C, Takahashi M, Goncalves J, Ritter J, et al. Gene expression profiles in children undergoing cardiac surgery for right heart obstructive lesions. *J Thorac Cardiovasc Surg.* 2003; 127:746-754.

[xi] Beltrmi A P, Barlucchi L, Torella D, Baker M, Limana F, Chimenti S, et al. Adult cardiac stem cells are multipotent and support myocardial regeneration. *Cell.* 2003; 114:763-776.

[xii] Beltrami A P, Urbanek K, Leri A, Kajstura J, Nadal-Ginard B, Anversa, P. Adult cardiac stem cells are multipotent and support myocardial regeneration. *Cell.* 2003; 114: 763-776.

[xiii] Oh H, Schneider M D. Cardiac muscle plasticity in adult and embryo by heart-derived progenitor cells. *Ann N Y Acad Sci.* 2004; 1015:182-189.

[xiv] Anversa P, Nadal-Ginard B. Myocyte renewal and ventricular remodelling. *Nature.* 2002; 415:240-243.

[xv] Hannigan G E, Leung-Hagesteijn C, Fitz-Gibbon L, Coppolino M G, Radeva G, Filmus J, et al. Regulation of cell adhesion and anchorage-dependent growth by a new beta 1-integrin-linked protein kinase. *Nature* 1996; 379:91-96.

[xvi] Hannigan G, Troussard A A, Dedhar S. Integrin-linked kinase: a cancer therapeutic target unique among its ILK. *Nat Rev Cancer.* 2005; 5:51-63.

[xvii] Troussard A A, Dedhar S. Conditional knock-out of integrin-linked kinase demonstrates an essential role in protein kinase B/Akt activation. *J Biol Chem.* 2003; 278:22374-22378.

[xviii] Leung-Ragesteijn C, Mahendra A, Naruszewicz I, Hannigan G E. Modulation of integrin signal transduction by ILKAP, a protein phosphatase 2C associating with the integrin-linked kinase, ILKI. *EMBO J.* 2001; 20:2160-70.

[xix] Choi J H, Hur J. Yoon C E, Kim J R, Lee C S, Young S W, et al. Augmentation of Therapeutic Angiogenesis Using Genetically Modified Human Endothelial Progenitor Cells with Altered Glycogen Synthase Kinase-3{beta} Activity. *J Biol Chem.* 2004; 279: 49430-49438.

[xx] Eckfeldt C E, Mendenhall E M Verfallie C M. The molecular repertoire of the 'Almighty' stem cell. *Nat Rev Mol Cell Biol.* 2005; 2-13.

xxi Reya T, Clevers H. Wnt signalling in stem cells and cancer. *Nature.* 2005; 434:843-850.

[xxii] Liu B Y, McDermott S P, Khwaja S S, Alexander C M. The transforming activity of Wnt effectors correlates with their ability to induce the accumulation of mammary progenitor cells. *Proc Natl Acad Sci USA.* 2004; 101:4158-4163.

[xxiii] Zechner D, Fujita Y, Hulsken J, Muller T, Walther I, Taketo M M, et al. β-Catenin signals regulate cell growth and the balance between progenitor cell expansion and differentiation in the nervous system. *Dev Biol.* 2003; 258: 406-418.

[xxiv] Austin T W, Solar G P, Ziegler F C, Liem L, Matthews W. A role for the Wnt gene family in hematopoiesis: expansion of multilineage progenitor cells. *Blood.* 1997; 89:3624-3635.

[xxv] Reya T, Duncan A W, Alles L, Domen J, Scherer D C, Willert K. A role for Wnt signalling in self-renewal of haematopoietic stem cells. *Nature.* 2003; 423:409-414.

[xxvi] Coles J G, Takahashi M, Dai X, Boscarino C, Hannigan G. Cardioprotective stress response in the human fetal heart. *JTCVS.* 2005; 129:112-136.

[xxvii] Miller M G, Hannigan G E. Integrin-linked kinase is a positive mediator of L6 myoblast differentiation. *Biochem Biophys Res Commun.* 2003; 310:796-803.

[xxviii] Milosevic J, Storch A, Schwarz J. Cyropreservation does not affect proliferation and multipotency of murine neural precursor cells. *Stem Cells.* 2005; 23:681-688.

[xxix] Lee A, Kessler J D, Read T-A, Kaiser C, Coreil D, Huttner W B, et al. Isolation of neural stem cells from the postnatal cerebellum. *Nature Neuroscience.* 2005; 8:723-729.

[xxx] Beltrami A P, Urbanek K, Leri A, Kajstura J, Nadal-Ginard B, Anversa P. Adult cardiac stem cells are multipotent and support myocardial regeneration. *Cell.* 2003; 114:763-776.

[xxxi] Messina E, De Angelis L, Frati G, Morrone S, Chimenti S, Fiordaliso F, et al. Isolation and expansion of adult cardiac stem cells from human and murine heart. *Circ Res.* 2004; 95:911-921.

[xxxii] Matsuura K, Komuro I. Adult cardiac Sca-1-positive cells differentiate into beating cardiomyocytes. *J Biol Chem.* 2004; 279:11384-11391.

[xxxiii] Araki H, Mahmud N, Milhem M, Nunez R, Xu M, Beam C A, et al Expansion of human umbilical cord blood SCID-repopulating cells using chromatin-modifying agents. *Exp Hematol.* 2006; 34:140-149.

[xxxiv] Novak A, Dedhar S. Signaling through beta-catenin and Lef/Tcf. *Cell Mol Life Sci.* 1999; 56:523-537.

[xxxv] Novak A, Dedhar S. Cell adhesion and the integrin-linked kinase regulate the LEF-1 and beta-catenin signaling pathways. *Proc Natl Acad Sci USA.* 1998; 5:437-4379.

[xxxvi] Xie D, Yin D, Tong X, O'Kelly J, Mori A, Miller C, et al. Cyr61 is overexpressed in gliomas and involved in integrin-linked kinase-mediated Akt and beta-catenin-TCF/Lef signaling pathways. *Cancer Res.* 2004; 64:1987-1996.

[xxxvii] Tan C, Dedhar S. Inhibition of integrin linked kinase (ILK) suppresses beta-catenin-Lef/Tcf-dependent transcription and expression of the E-cadherin repressor, snail, in APC−/−human colon carcinoma cells. *Oncogene.* 2001; 20:133-140.

xxxviii Kumar A S, Naruszewicz I, Wang P, Leung-Hagesteijn C, Hannigan G E. ILKAP regulates ILK signaling and inhibits anchorage-independent growth. *Oncogene.* 2004; 23:3454-3461.

xxxix Beltrami A P, Barlucchi L, Torella D, Baker M, Limana F, Chimenti S, et al. Adult cardiac stem cells are multipotent and support myocardial regeneration. *Cell.* 2003; 114:763-776.

xl Messina E, De Angelis L, Frati G, Morrone S, Chimenti S, Fiordaliso F, et al. Isolation and expansion of adult cardiac stem cells from human and murine heart. *Circ Res.* 2004; 95:911-921.

xli Laugwitz K L, Moretti A, Lam J, Gruber P, Chen A, Woodard S, et al. Postnatal isl1+cardioblasts enter fully differentiated cardiomyocyte lineages. *Nature.* 2005; 433:647-653.

xlii Yamataka A, Ohshiro K, Kobayashi E, Lane G J, Yamataka T, Fujiwara T, et al. Abnormal distribution of intestinal pacemaker (C-KIT-positive) cells in an infant with chronic idiopathic intestinal pseudoobstruction. *J Pediatr Surg.* 1998; 33:859-862.

xliii Troussard A A, Tan C, Yoganathan N, Dedhar S. Cell-extracellular matrix interactions stimulate the AP-1 transcription factor in an integrin-linked kinase- and glycogen synthase kinase 3-dependent manner. *Mol Cell Biol.* 1999; 19:7420-7427.

xliv Persad S, Attwell S, Gray V, Delcommenne M, Troussard A, Saughera J, et al. Inhibition of integrin-linked kinase (LK) suppresses activation of protein kinase B/Akt and induces cell cycle arrest and apoptosis of PTEN-mutant prostate cancer cells. *Proc Natl Acad Sci USA.* 2000; 97:3207-3212.

xlv Troussard A A, Mawji N M, Ong C, Mui A, St-Arnaud R, Dedhar S. Conditional knock-out of integrin-linked kinase demonstrates an essential role in protein kinase B/Akt activation. *J Biol Chem.* 2003; 278:22374-22378.

xlvi Gerber H P, Malik A K, Solar G P, Sherman D, Liang X H, Meng G, et al. VEGF regulates haematopoietic stem cell survival by an internal autocrine loop mechanism. *Nature* 2002; 417:954-958.

What is claimed is:

1. A method for inducing beneficial human cardiac hypertrophy in an individual by way of the integrin linked kinase (ILK) pathway comprising the following steps:
   (a) culturing in vitro one or more dissociated heart tissue cells derived from a first individual;
   (b) infecting the one or more dissociated heart tissue cells with an adenovirus vector encoding an integrin linked kinase (ILK) gene; and
   (c) administering the one or more infected heart tissue cells to a second individual.

2. The method of claim 1 which further includes eliciting an overexpression of ILK in the one or more infected heart tissue cells.

3. The method of claim 1, wherein the culturing step (a) comprises culturing the dissociated heart tissue cells in serum-free medium supplemented with fetal bovine serum.

4. The method of claim 1, further comprising the step of (d) dissociating a heart tissue sample derived from the individual to form the one or more dissociated heart tissue cells comprising enzymatic digestion with trypsin and/or Type II collagenase, wherein step (d) is performed prior to step (a).

5. The method of claim 4, wherein the heart tissue derived from the individual is further minced and washed before enzymatic digestion during step (d).

6. The method of claim 4, further comprising the step of (e) removing fibroblasts from the one or more dissociated heart tissue cells, wherein step (e) is performed prior to step (a) but after step (d).

7. The method of claim 6, wherein step (e) is performed by culturing the one or more dissociated heart tissue cells in a pre-coated plate or dish and removing the supernatant of the culture from the pre-coated plate or dish for culturing in step (a).

8. The method of claim 1, wherein the infecting step (b) is performed after the culture in step (a) reaches a confluency of between about 50% and about 70%.

9. The method of claim 1, wherein the infecting step (b) is performed after culturing the one or more dissociated heart tissue cells for about 2 to 4 days in step (a).

10. The method of claim 1, wherein the infecting step (b) is performed with a multiplicity of infection of between about 1.5 and 2.0.

11. The method of claim 1, wherein the one or more heart tissue cells are infected in a serum-free medium supplemented with fetal bovine serum during step (b).

12. The method of claim 1, wherein the one or more heart tissue cells are infected with 10 pfu/ml of adenovirus vector during step (b).

13. The method of claim 1, wherein the adenovirus comprises a replication-deficient serotype 5 adenovirus.

14. The method of claim 1, wherein the integrin linked kinase (ILK) gene is a human ILK gene.

15. The method of claim 1, wherein the integrin linked kinase (ILK) gene is a wild-type human ILK gene.

16. The method of claim 1, wherein the one or more heart tissue cells infected with the adenovirus vector encoding the integrin linked kinase (ILK) gene in step (b) have a greater number of c-Kit-positive cells compared to heart tissue cells infected with an empty adenovirus vector that does not encode an integrin linked kinase (ILK) gene.

17. The method of claim 1, wherein the one or more heart tissue cells infected with the adenovirus vector encoding the integrin linked kinase (ILK) gene in step (b) have an increase in GTP-bound Rac-1 compared to heart tissue cells infected with an empty adenovirus vector that does not encode an integrin linked kinase (ILK) gene.

18. The method of claim 17, wherein the increase in GTP-bound Rac-1 in the one or more heart tissue cells infected with the adenovirus vector encoding the integrin linked kinase (ILK) gene in step (b) is blocked by treatment with KP-392.

19. The method of claim 1, wherein the one or more heart tissue cells infected with the adenovirus vector encoding the integrin linked kinase (ILK) gene in step (b) have an increase in GTP-bound Cdc42 compared to heart tissue cells infected with an empty adenovirus vector that does not encode an integrin linked kinase (ILK) gene.

20. The method of claim 19, wherein the increase in GTP-bound Cdc42 in the one or more heart tissue cells infected with the adenovirus vector encoding the integrin linked kinase (ILK) gene in step (b) is blocked by treatment with KP-392.

21. The method of claim 1, wherein the one or more heart tissue cells infected with the adenovirus vector encoding the integrin linked kinase (ILK) gene in step (b) form a greater number of anchorage-independent primary cardiospheres when cultured in a medium containing fibroblast growth factor (FGF) and epidermal growth factor (EGF) in comparison to heart tissue cells infected with an empty adenovirus vector that does not encode an integrin linked kinase (ILK) gene.

22. The method of claim 1, wherein the subject first individual and the second individual are human.

23. The method of claim 22, wherein the first individual and the second individual are the same person.

24. The method of claim 1, wherein the one or more infected heart tissue cells are administered to the heart of the second individual in step (c).

25. A method for inducing beneficial human cardiac hypertrophy in an individual by way of the integrin linked kinase (ILK) pathway comprising the following steps:
   (a) culturing in vitro one or more dissociated heart tissue cells derived from a first individual;
   (b) infecting the one or more dissociated heart tissue cells with an adenovirus vector encoding an integrin linked kinase (ILK) gene; and
   (c) transplanting the one or more infected heart tissue cells to the heart of a second individual.

26. The method of claim 25, wherein the first individual and the second individual are the same individual.

27. The method of claim 25, wherein the first individual and the second individual are human.

28. A method for inducing beneficial human cardiac hypertrophy in an individual by way of the integrin linked kinase (ILK) pathway comprising the following steps:
   (a) infecting one or more dissociated heart tissue cells cultured in vitro from a first individual with an adenovirus vector encoding an integrin linked kinase (ILK) gene; and
   (b) administering the one or more infected heart tissue cells to a second individual.

29. The method of claim 28, wherein the first individual and the second individual are the same individual.

30. The method of claim 28, wherein the first individual and the second individual are human.

31. A method for inducing beneficial human cardiac hypertrophy in an individual by way of the integrin linked kinase (ILK) pathway comprising the following steps:
   (a) culturing in vitro one or more dissociated heart tissue cells derived from the individual;
   (b) infecting the one or more dissociated heart tissue cells with an adenovirus vector encoding an integrin linked kinase (ILK) gene; and
   (c) administering the one or more infected heart tissue cells to the individual.

32. The method of claim 31, wherein the individual is a human.

33. A method for inducing beneficial human cardiac hypertrophy in a second individual by way of the integrin linked kinase (ILK) pathway comprising the following steps:
   (a) culturing in vitro one or more dissociated heart tissue cells derived from a first individual;
   (b) infecting the one or more dissociated heart tissue cells with an adenovirus vector encoding an integrin linked kinase (ILK) gene; and
   (c) administering the one or more infected heart tissue cells to the second individual.

34. The method claim 33, wherein the first individual and the second individual are the same individual.

35. The method of claim 33, wherein the first individual and the second individual are human.

* * * * *